US012770252B2

(12) United States Patent
Wilson et al.

(10) Patent No.: US 12,770,252 B2
(45) Date of Patent: Oct. 20, 2026

(54) PREDICTION OF STENT EXPANSION USING FINITE ELEMENT MODELING AND MACHINE LEARNING

(71) Applicants: Case Western Reserve University, Cleveland, OH (US); Florida Institute of Technology, Melbourne, FL (US); University Hospitals Cleveland Medical Center, Cleveland, OH (US); University of South Florida, Tampa, FL (US)

(72) Inventors: David L. Wilson, Cleveland Heights, OH (US); Yazan Gharaibeh, Irbid (JO); Juhwan Lee, Westlake, OH (US); Linxia Gu, Melbourne, FL (US); Pengfei Dong, Melbourne, FL (US); Sadeer Al-Kindi, Lyndhurst, OH (US); Hiram Bezerra, Tampa, FL (US)

(73) Assignees: Case Western Reserve University, Cleveland, OH (US); Florida Institute of Technology, Melbourne, FL (US); University Hospitals Cleveland Medical Center, Cleveland, OH (US); University of South Florida, Tampa, FL (US)

( * ) Notice: Subject to any disclaimer, the term of this patent is extended or adjusted under 35 U.S.C. 154(b) by 499 days.

(21) Appl. No.: 18/332,950

(22) Filed: Jun. 12, 2023

(65) Prior Publication Data

US 2024/0169524 A1 May 23, 2024

Related U.S. Application Data

(60) Provisional application No. 63/427,476, filed on Nov. 23, 2022.

(51) Int. Cl.
*G06T 7/00* (2017.01)
*A61B 5/02* (2006.01)

(52) U.S. Cl.
CPC ........ *G06T 7/0012* (2013.01); *A61B 5/02007* (2013.01); *G06T 2207/10101* (2013.01);
(Continued)

(58) Field of Classification Search
None
See application file for complete search history.

(56) References Cited

U.S. PATENT DOCUMENTS

| | | | | |
|---|---|---|---|---|
| 2006/0058592 A1* | 3/2006 | Bouma | ................ | A61B 5/0059 600/301 |
| 2011/0093243 A1* | 4/2011 | Tawhai | ................ | G06T 7/0012 703/2 |

(Continued)

FOREIGN PATENT DOCUMENTS

| | | | | |
|---|---|---|---|---|
| WO | WO-2023133355 A1 * | 7/2023 | ............... | A61B 1/06 |
| WO | WO-2024023794 A1 * | 2/2024 | ........... | A61B 8/5223 |

*Primary Examiner* — Miya J Cato
(74) *Attorney, Agent, or Firm* — Eschweiler & Potashnik, LLC

(57) ABSTRACT

The present disclosure, in some embodiments, relates to a method of determining a stent effectiveness. The method includes accessing a pre-stent intravascular image of a blood vessel of a patient. One or more pre-stent label volumes of the blood vessel are determined and one or more treatment variables associated with the pre-stent intravascular image are determined. One or more FEM-mimic simulations are generated by applying a first deep learning model to the one or more pre-stent label volumes and the one or more treatment variables. The one or more FEM-mimic simulations are used to determine a stent effectiveness metric.

20 Claims, 13 Drawing Sheets

(52) U.S. Cl.
CPC ............... *G06T 2207/20081* (2013.01); *G06T 2207/30101* (2013.01)

(56) References Cited

U.S. PATENT DOCUMENTS

| | | | | |
|---|---|---|---|---|
| 2015/0297373 | A1* | 10/2015 | Schmitt | A61F 2/86<br>623/1.16 |
| 2015/0374243 | A1* | 12/2015 | Itu | A61B 5/7275<br>703/2 |
| 2021/0125337 | A1* | 4/2021 | Wilson | G06N 3/08 |
| 2023/0187054 | A1* | 6/2023 | Thibault | G06T 17/00 |
| 2023/0223152 | A1* | 7/2023 | Wilson | G16H 30/40<br>382/128 |
| 2024/0156529 | A1* | 5/2024 | Rozen | G06T 7/10 |

* cited by examiner

1106

1108

1110

1200

1600

| Features | # of features |
|---|---|
| First Order Statistics | 19 |
| Shape-based (3D) | 16 |
| Shape-based (2D) | 10 |
| Gray Level Cooccurrence Matrix | 24 |
| Gray Level Run Length Matrix | 16 |
| Gray Level Size Zone Matrix | 16 |
| Neighboring Gray Tone Difference Matrix | 5 |
| Gray Level Dependence Matrix | 14 |

PREDICTION OF STENT EXPANSION USING FINITE ELEMENT MODELING AND MACHINE LEARNING

CROSS REFERENCE TO RELATED APPLICATIONS

This application claims the benefit of priority from U.S. Provisional Patent Application No. 63/427,476 filed Nov. 23, 2022 and entitled "PREDICTION OF STENT EXPANSION USING FINITE ELEMENT MODELING AND MACHINE LEARNING", the contents of which are incorporated herein by reference in their entirety.

FEDERAL FUNDING INFORMATION

This invention was made with government support under HL143484 awarded by the National Institutes of Health. The government has certain rights in the invention.

BACKGROUND

Calcification is the accumulation of calcium salts in a body tissue. It normally occurs in the formation of bone, but calcium can also be deposited abnormally in soft tissue. For example, calcium containing plaque can collect in a heart's two main arteries (e.g., coronary arteries), making it difficult for blood to travel through the arteries. The build-up of plaque in the coronary arteries is one of the strongest indicators for complications such as heart attacks, strokes, etc.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Figure 1:
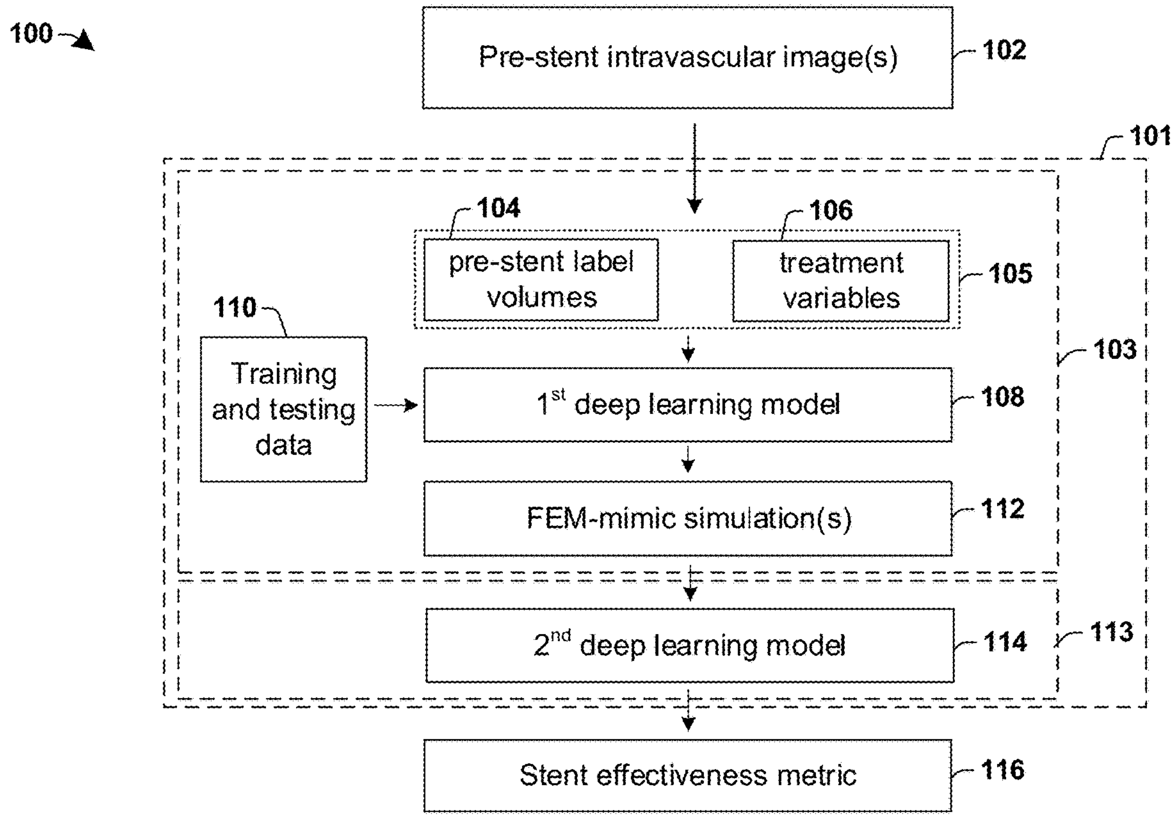
FIG. 1 illustrates a block diagram corresponding to some embodiments of a method and/or apparatus of determining a stent effectiveness using a deep learning model that mimics finite element modeling (FEM) based on one or more pre-stent intravascular images.

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

Arteries are blood vessels that carry blood throughout your body. Healthy arteries have smooth inner walls and blood flows through them easily. However, over time, plaque can build up on the inner walls of arteries. Plaque is a waxy substance that includes fatty substances, cholesterol, calcium, waste products from cells, and a blood-clotting material known as fibrin. Plaque buildup can clog arteries, thereby reducing blood flow through an artery or, in some instances, blocking the artery altogether. A clogged artery greatly increases a likelihood of a heart attack, stroke, and/or even death.

A healthy lifestyle is important to prevent and/or manage clogged arteries. However, sometimes lifestyle choices and/or medications are not sufficient to prevent plaque buildup. In such cases, surgical procedures may be used to treat a patient. One common surgical procedure used to treat plaque buildup is placement of a stent. A stent is a small tube-like structure that may be inserted into an artery to maintain adequate blood flow through the artery. However, stent placement is not always successful. It has been appreciated that calcification lesions within the atherosclerotic tissue of a blood vessel may be a cause of stent placement failure, as calcification lesions may impair device delivery and/or inhibit stent expansion. For example, when a stent is implanted into a blood vessel having atherosclerotic tissue that has hardened due to the presence of calcification lesions, it is often difficult to fully expand the implanted stent (e.g., even using a high-pressure balloon).

When calcification lesions are present, an interventional cardiologist has many choices to make, including whether to apply a pre-treatment plaque modification device (e.g., atherectomy or intravascular lithotripsy), whether to perform balloon pre-treatment, a stent length and/or diameter, a stent location, a number of stents, a balloon size, a balloon pressure, etc. These choices may be affected by such factors as distal artery size, vessel taper, and an extent (e.g., arc length, thickness, etc.) of a calcification lesion. Poor choices by the interventional cardiologist can lead to negative consequences such as inadequate stent deployment, malapposed struts, a ruptured balloon, vascular tissue dissection, a ruptured blood vessel, a perforated blood vessel wall, and/or the like.

In some embodiments, the present disclosure relates to a method and/or apparatus to determine an effectiveness of a stent placement procedure using a deep learning model that mimics finite element modeling (FEM) based on one or more pre-stent intravascular images. The method may be performed by accessing a pre-stent intravascular image of a patient's blood vessel. One or more pre-stent label volumes of the blood vessel and one or more treatment variables associated with the blood vessel are determined. A first deep learning model uses the one or more pre-stent label volumes and the one or more treatment variables to generate FEM-mimic simulations that respectively mimic one or more finite element models (FEMs) of the blood vessel. A stent effectiveness is subsequently determined based upon the FEM-mimic simulations. The use of a deep learning model to mimic FEMs allows for the disclosed method to achieve a high degree of accuracy without a high computation cost and large time typically associated with finite element modeling. By determining a stent effectiveness to a high degree of accuracy, an interventional cardiologist is able to quickly make better choices that minimize negative consequences (e.g., a ruptured blood vessel, vascular tissue dissection, etc.) and achieve more favorable results for a patient.

FIG. 1 illustrates a block diagram 100 corresponding to some embodiments of a stent prediction apparatus 101 configured to determine a stent effectiveness using a deep learning model that mimics finite element modeling (FEM).

The stent prediction apparatus 101 is configured to access one or more pre-stent intravascular images 102 (e.g., images taken before insertion of a stent) of a blood vessel of a patient. The stent prediction apparatus 101 is configured to operate upon the one or more pre-stent intravascular images 102 with deep learning that attempts to mimic FEM and generate one or more FEM-mimic simulations 112. The one or more FEM-mimic simulations 112 can be subsequently used to generate a stent effectiveness metric 116 that quantifies a likelihood that a stent will properly expand within the blood vessel. In some embodiments, the stent prediction apparatus 101 comprises a first stage 103 and a second stage 113 downstream of the first stage 103.

The first stage 103 is configured to determine one or more pre-stent metrics 105 that describe the one or more pre-stent intravascular images 102. In some embodiments, the one or more pre-stent metrics 105 may comprise one or more pre-stent label volumes 104 and one or more treatment variables 106. The one or more pre-stent label volumes 104 may comprise a lumen and a calcification (e.g., a segmentation of a lumen and a calcification) before a stent is inserted into the blood vessel. The one or more treatment variables 106 may comprise a balloon size, a balloon pressure, and/or the like.

The first stage 103 comprises a first deep learning model 108 configured to receive the one or more pre-stent metrics 105. The first deep learning model 108 is configured to utilize the one or more pre-stent metrics 105 to mimic FEM and to generate one or more FEM-mimic simulations 112 that corresponds to how the blood vessel will respond to the insertion and expansion of a stent. For example, the first deep learning model 108 may utilize the one or more pre-stent label volumes 104 and the one or more treatment variables 106 to generate one or more FEM-mimic simulations 112 comprising a displacement field showing changes in positions of blood vessel components in response to the insertion and expansion of the stent at a given set of treatment variables (e.g., at a given balloon and inflation pressure). In some additional embodiments, the one or more FEM-mimic simulations 112 may also include an inflated label volume. The inflated label volume may include a predicted lumen size and/or shape, a predicted calcification lesion size and/or shape, as well as any shape changes in the vessel wall.

In some embodiments, the first deep learning model 108 is trained and tested against training and testing data 110 including a plurality of finite element models (FEMs). By training the first deep learning model 108 against FEMs, the first deep learning model 108 is able to generate FEM-mimic simulations 112 that have a high correlation with FEMs.

The second stage 113 is configured to utilize the one or more FEM-mimic simulations 112 to determine the stent effectiveness metric 116. In some embodiments, the stent effectiveness metric 116 may comprise stress/strain maps of the blood vessel, a stent expansion index (SEI), a minimum expansion index (MEI), and/or the like. In some embodiments the second stage 113 may comprise a second deep learning model 114 that is configured to utilize the one or more FEM-mimic simulations 112 (e.g., the displacement field and/or the inflated label volume) to generate the stent effectiveness metric 116.

Due to the computational complexity of finite element modeling (FEM), it is difficult to use FEM to provide for a quick and easy prognostic analysis of a stent effectiveness. However, by using deep learning to mimic FEM the disclosed stent prediction apparatus 101 is able to achieve a prognosis having the high accuracy of FEM without the computational complexity (e.g., relatively long computation time). Therefore, the disclosed stent prediction apparatus 101 is able to achieve good results based on one or more pre-stent intravascular images, allowing health care professionals to make quick and informed decisions on stent treatment (e.g., the disclosed stent prediction apparatus 101 can generate a stent effectiveness metric 116 within a few seconds). For example, if based on the stent effectiveness metric 116 an interventional cardiologist does not think a stent will be sufficiently expanded, the interventional cardiologist can treat a calcified lesion with plaque modification (e.g., atherectomy, scoring/cutting balloon, shockwave, or using very high balloon pressures) prior to stent insertion.

It will be appreciated that the disclosed methods and/or block diagrams may be implemented as computer-executable instructions, in some embodiments. Thus, in one example, a computer-readable storage device (e.g., a non-transitory computer-readable medium) may store computer executable instructions that if executed by a machine (e.g., computer, processor) cause the machine to perform the disclosed methods and/or block diagrams. While executable instructions associated with the disclosed methods and/or block diagrams are described as being stored on a computer-readable storage device, it is to be appreciated that executable instructions associated with other example disclosed methods and/or block diagrams described or claimed herein may also be stored on a computer-readable storage device. In some embodiments, the computer-executable instructions may be implemented within a software package, so as to allow a health care professional to utilize the disclosed methods and/or block diagrams through the software package.

Figure 2:
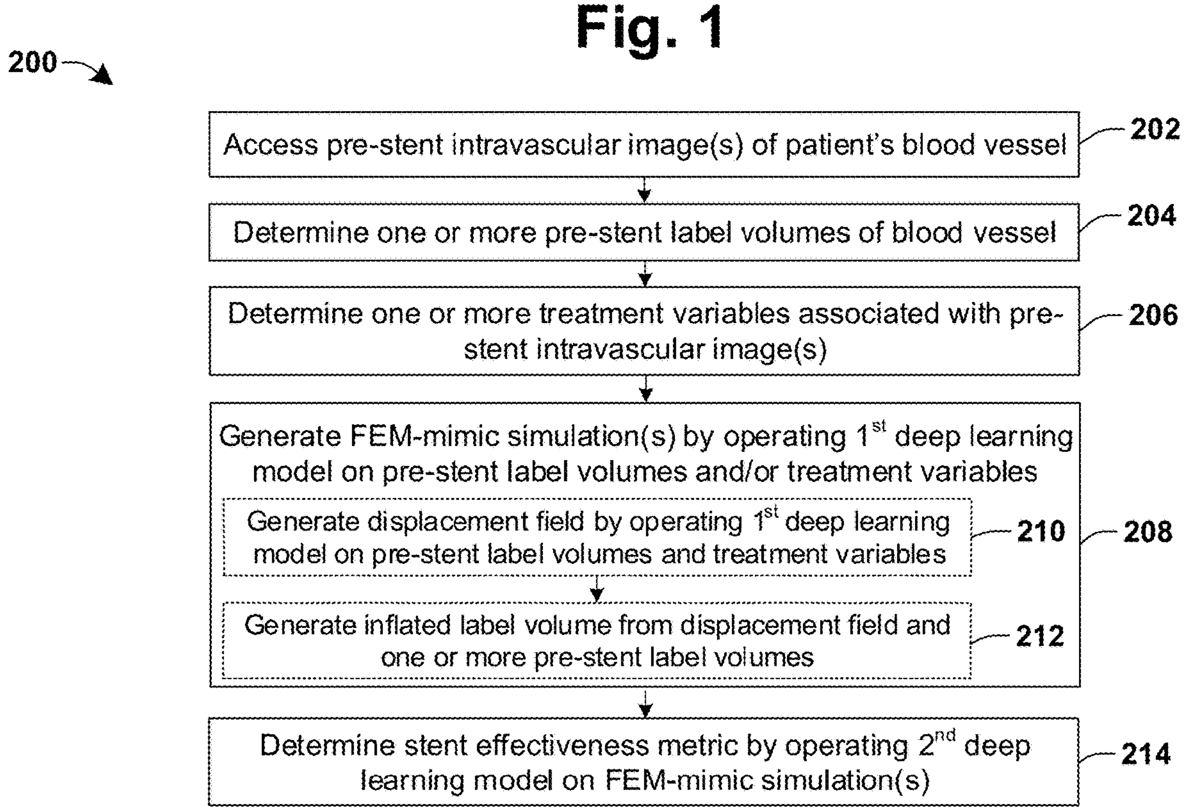
FIG. 2 illustrates a method for determining a stent effectiveness using a deep learning model that mimics FEM based on one or more pre-stent intravascular images.

FIG. 2 illustrates a method 200 for determining a stent effectiveness metric using a deep learning model that mimics finite element modeling (FEM) based on one or more pre-stent intravascular images.

While the disclosed method 200 is illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At act 202, one or more pre-stent intravascular images of a patient's blood vessel are accessed. In some embodiments, the one or more pre-stent intravascular images may comprise intravascular optical coherence tomography (IVOCT) images taken of a patient's blood vessel without a stent.

At act 204, one or more pre-stent label volumes of the blood vessel are determined from the one or more pre-stent intravascular images.

At act 206, one or more treatment variables associated with the one or more pre-stent intravascular images (e.g., label volume, balloon size, pressure, etc.) are determined.

At act 208, one or more FEM-mimic simulations are generated by operating a first deep learning model on the one or more pre-stent label volumes and/or the one or more treatment variables. In some embodiments, the one or more FEM-mimic simulations may be generated according to acts 210-212.

At act 210, a displacement field is generated by operating a first deep learning model on the one or more pre-stent label volumes and the one or more treatment variables.

At act 212, an inflated label volume is determined from the displacement field and the one or more pre-stent label volumes.

At act 214, a stent effectiveness metric is generated by operating a second deep learning model on the one or more FEM-mimic simulations (e.g., the displacement field and/or the inflated label volume).

Figure 3:
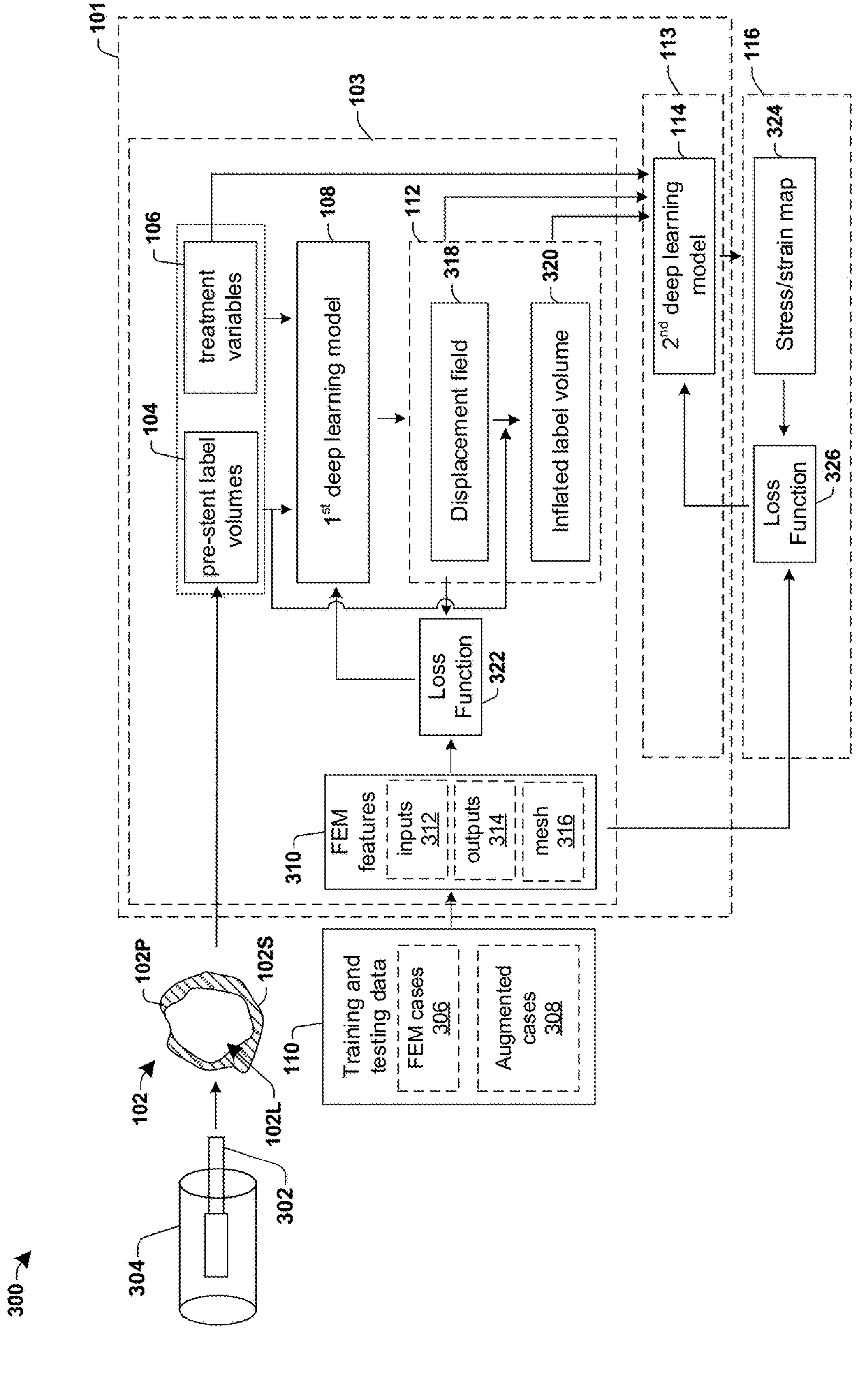
FIG. 3 illustrates a block diagram corresponding to some additional embodiments of a method and/or apparatus of determining a stent effectiveness using a deep learning model that mimics FEM.

FIG. 3 illustrates a block diagram 300 corresponding to some additional embodiments of a stent prediction apparatus configured to determine a stent effectiveness using a deep learning model that mimics FEM.

The stent prediction apparatus 101 is configured to access an image volume comprising one or more pre-stent intravascular images 102 of a blood vessel of one or more patients. The one or more pre-stent intravascular images 102 of the blood vessel may comprise a lumen 102L and one or more calcification lesions 102P arranged along a sidewall 102S of the blood vessel.

In some embodiments, the one or more pre-stent intravascular images 102 may comprise a pre-stent intravascular optical coherence tomography (IVOCT) image generated by an IVOCT imaging system. In such embodiments, the one or more pre-stent intravascular images 102 may be generated by inserting a catheter 302 into one or more blood vessels 304 of the one or more patients. Unlike an intravascular ultrasound tool, an IVOCT imaging system can penetrate calcification lesions to visualize their thickness, thereby allowing for a more complete assessment of the calcification lesions. Furthermore, the IVOCT imaging system is able to provide a detailed evaluation of a morphology of the calcifications. Therefore, IVOCT images are a useful tool for identifying lesion severity, reference vessel size, lesion length, an extent of calcification, etc., in comparison with other imaging options (e.g., angiographic imaging).

The stent prediction apparatus 101 comprises a first stage 103 and a second stage 113 downstream of the first stage 103. The first stage 103 comprises a first deep learning model 108 that is configured to utilize one or more pre-stent metrics 105 to mimic FEM simulations and generate one or more FEM-mimic simulations 112. The one or more pre-stent metrics 105 may comprise one or more pre-stent label volumes 104 and one or more treatment variables 106. In some additional embodiments, the one or more pre-stent label volumes 104 may comprise a segmented lumen and a calcification lesion input to the first deep learning model 108 as binary inputs. In such embodiments (not shown), the one or more pre-stent metrics 105 may also comprise the one or more pre-stent intravascular images 102 (e.g., providing the one or more pre-stent intravascular images 102 as inputs to the first deep learning model 108 gives the binary inputs a context).

The one or more FEM-mimic simulations 112 may comprise a displacement field 318 and an inflated label volume 320 showing changes in positions of blood vessel components in response to the insertion and expansion of the stent at a given set of treatment variables (e.g., at a given balloon and inflation pressure). In some embodiments, the first deep learning model 108 may track a displacement of each corner of a tetrahedral mesh overlaid on a blood vessel to obtain a dense field of displacements. In some embodiments, the dense field of displacements may be further processed to obtain one or more FEM-mimic simulations 112 comprising a displacement field 318 on a regular Cartesian grid. In some additional embodiments, the first stage 103 may be configured to utilize the displacement field 318 to transform (e.g., re-shape) the one or more pre-stent label volumes 104 into one or more FEM-mimic simulations 112 comprising an inflated label volume 320. The inflated label volume 320 provides a predicted lumen and any shape changes in a wall of the blood vessel due to insertion of a stent. In some embodiments, the first deep learning model 108 may comprise a network used for 3D one-shot image registration (e.g., a 3D U-Net modified to accept the input, pre-stent label volume and scaler treatment variables).

In some embodiments, the first deep learning model 108 is trained and tested to mimic FEM simulations using training and testing data 110 comprising FEM cases 306. In some embodiments, the FEM cases 306 may comprise at least 405 FEMs from ex vivo data (e.g., 45-lesion-meshes× 9-sizes/pressures) and 720 FEM predictions from in vivo data (e.g., 80-lesion-meshes×actual treatment size/pressure+8 other treatment plans), giving a total of 1,125 FEM predictions.

In some embodiments, the training and testing data 110 may further comprise augmented FEM cases 308. The augmented FEM cases 308 may comprise FEM cases that have been modified by rotation of a blood vessel, displacement of a blood vessel, and/or small perturbations of a pressure and/or a calcification. For example, the augmented FEM cases 308 may be generated by rotating both the input label volume and the FEM predictions about an IVOCT center in increments of 20 degrees to generate new training/testing data, by causing small displacements (e.g., in an x-direction and or a y-direction perpendicular to a vessel length) of the volume, by generating voxel-sized changes in boundaries on a random basis, and/or the like. In some embodiments, the data augmentations may be performed randomly and stacked (e.g., rotate by an angle and then displace in an instantiation).

During training of the first deep learning model 108, the one or more FEM-mimic simulations 112 will be evaluated through comparison to FEMs within the training and testing data 110. For example, the first stage 103 may be configured to collect FEM features 310 from the training and testing data 110 and compare the collected FEM features 310 to features of the one or more FEM-mimic simulations 112. In some embodiments, the FEM features 310 may comprise inputs 312 (e.g., label volume, balloon size, pressure, etc.), outputs 314 (e.g., FEM-predicted output label volume, stress, strain, displacement field, etc.), and/or a mesh 316 of tetrahedral elements before and after balloon inflation.

In some embodiments, the first stage 103 may comprise a first loss function 322 (e.g., a root mean square (RMS) error or a variant) between the displacement field 318 and the training and testing data 110. In such embodiments, the first loss function 322 is configured to provide feedback to the first deep learning model 108 based upon a comparison between the displacement field 318 and the training and testing data 110. In some embodiments, inflated label volumes of the one or more FEM-mimic simulations 112 may be compared to inflated label volumes of the training and testing data 110 using a voxel-wise confusion matrix and statistics. In some embodiments, stress/strain maps of the one or more FEM-mimic simulations 112 may be compared to stress/strain maps of the training and testing data 110 by computing coefficients of variation (COV) to the gold standard. In some embodiments, target performance metrics are DICE of greater than or equal to approximately 0.85 and COV of less than or equal to approximately 0.20.

The second stage 113 is configured to determine a stent effectiveness metric 116 based upon the one or more FEM-mimic simulations 112. In some embodiments, the second stage 113 comprises a second deep learning model 114 that is configured to generate a stent effectiveness metric 116 comprising stress/strain maps 324 using the displacement field 318, the inflated label volume 320, and treatment variables 106. By using a second deep learning model 114, the stress/strain maps 324 can be formed in a relatively quick time. In some embodiments, the second deep learning model 114 may comprise a modified 3D U-Net with modifications including input/output and fully connected layers. In some such embodiments, the second stage 113 may comprise a second loss function 326 (e.g., an RMS error or a variant). In such embodiments, the second loss function 326 is configured to provide feedback to the second deep learning model 114 based upon a comparison between the stress/strain maps 324 and the training and testing data 110.

Figure 4:
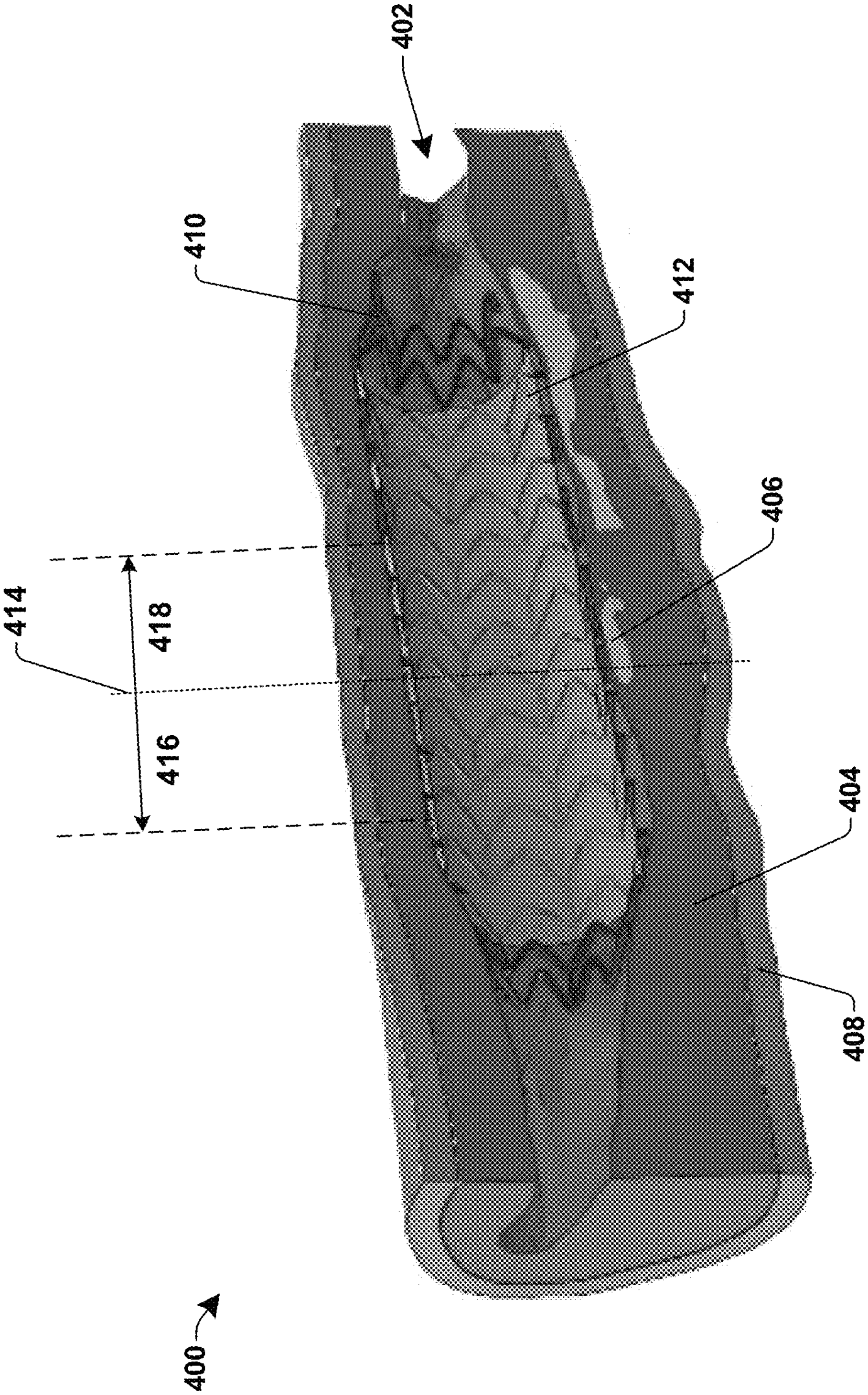
FIG. 4 illustrates some embodiments of a three-dimensional FEM of a blood vessel after dilation of a stent.

FIG. 4 illustrates some embodiments of a three-dimensional FEM model 400 of a blood vessel after dilation of a stent.

The three-dimensional FEM model 400 comprises a lumen 402 of a blood vessel, fibrotic tissue 404 surrounding the lumen 402, one or more calcified lesions 406 surrounded by the fibrotic tissue 404, and a vessel wall 408 surrounding the fibrotic tissue 404. A stent 410 is shown within the lumen 402. The stent 410 may be inserted into the blood vessel in a collapsed state surrounding a balloon 412. After insertion into the blood vessel, the balloon 412 is expanded so as to expand the stent 410 and increase a size of the lumen 402. The balloon 412 can be subsequently deflated and removed from the blood vessel, leaving the expanded stent 410 within the blood vessel.

In some embodiments, a disclosed first deep learning model (e.g., first deep learning model 108 of FIG. 3) may be configured to generate a segmental FEM-mimic simulation for a frame based upon inputs (e.g., additional label volumes) from surrounding frames. In some such embodiments, a segment may slide along a blood vessel and/or a calcified lesion to form a volumetric output. By performing a segmental FEM mimic simulation, a larger number of training cases may be collected thereby improving an accuracy of an output of the disclosed stent prediction apparatus.

In some embodiments the first deep learning model may generate a segmental FEM-mimic simulation corresponding to an output of a single center frame (taken along line 414) of a blood vessel from inputs collected from frames extending outward from the center frame a distance (e.g., +/−1.4 mm, +/−1.0 mm, or other similar values) in a first direction 416 and in a second direction 418. In other embodiments, the first deep learning model may generate a segmental FEM-mimic simulation corresponding to an output of a single center frame of a blood vessel from inputs collected from frames extending outward from the center frame (taken along line 414) a number of frames (e.g., +/−5 frames, +/−7 frames, +/−10 frames, or other similar values) in the first direction 416 and in the second direction 418.

Figure 5:
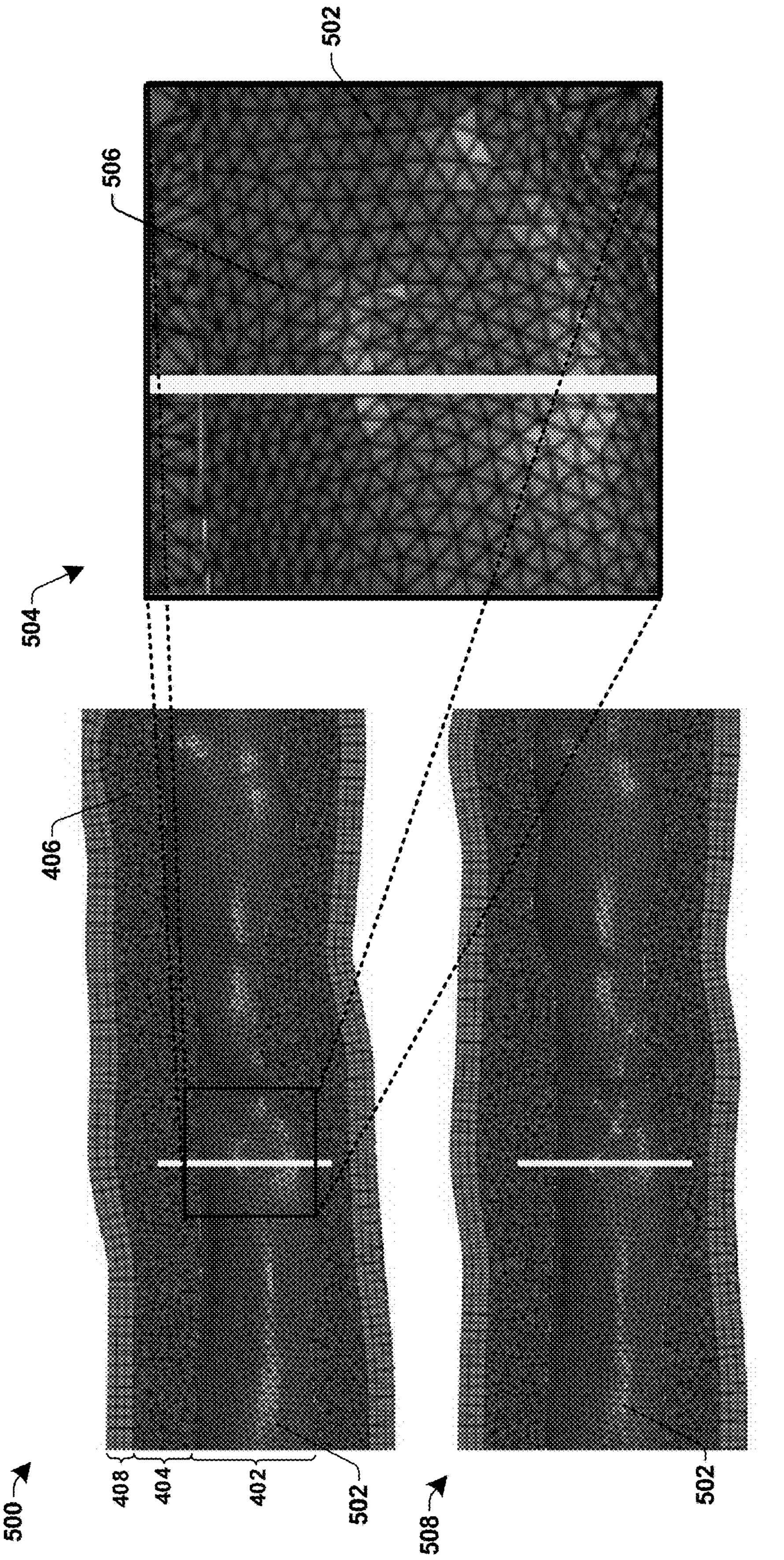
FIG. 5 illustrates some embodiments of a blood vessel illustrating a tetrahedral mesh before and after balloon inflation.

FIG. 5 illustrates cross-sectional views 500 of some embodiments of a blood vessel for a FEM simulation before and after balloon inflation.

Cross-sectional view 500 illustrates a FEM simulation comprising a tetrahedral mesh 502 before balloon inflation. The tetrahedral mesh 502 comprises a plurality of tetrahedral shaped segments in 3-D (e.g., triangular shaped segments in 2-D) arranged in a mesh that is overlaid on a lumen 402 of a blood vessel, fibrotic tissue 404 surrounding the lumen 402, one or more calcified lesions 406, and/or a vessel wall 408 surrounding the fibrotic tissue 404. Cross-sectional view 508 illustrates a FEM simulation comprising the tetrahedral mesh 502 after inflation of a balloon.

Cross-sectional view 504 illustrates an enlarged segment of the FEM simulation of cross-sectional view 500 with the tetrahedral mesh 502. As can be seen in cross-sectional view 504, the plurality of triangular shaped segments comprise corners 506. The corners 506 move during inflation of the balloon (e.g., between cross-sectional view 500 and cross-sectional view 508). The disclosed first deep learning model (e.g., first deep learning model 108 of FIG. 3) may be configured to track changes in positions of the corners 506 of the plurality of triangular shaped segments. The tracked changes in the positions of the corners 506 can be converted to a displacement vector that shows a change in position of a point within the blood vessel. The displacement vectors determined from the movement of the corners 506 of the plurality of triangular shaped segments collectively can be used to form a displacement field comprising displacement vectors that respectively represent a displacement from point the blood vessel due to inflation of the balloon.

Figure 6:
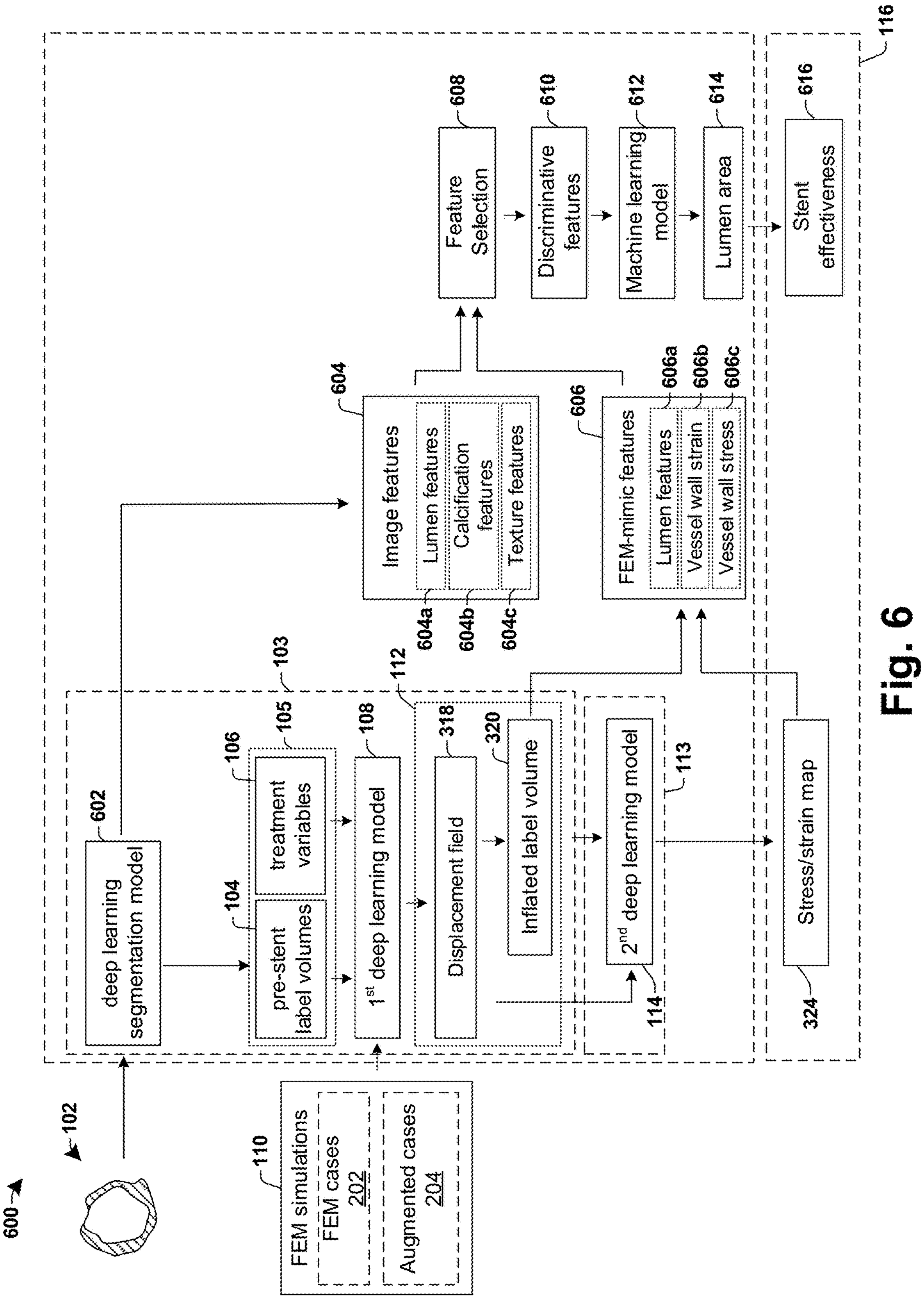
FIG. 6 illustrates a block diagram corresponding to some additional embodiments of a method and/or apparatus of determining a stent effectiveness using a deep learning model that mimics FEM.

FIG. 6 illustrates a block diagram 600 corresponding to some additional embodiments of a stent prediction apparatus configured to determine a stent effectiveness using a deep learning model that mimics FEM.

The stent prediction apparatus 101 is configured to access an image volume comprising one or more pre-stent intravascular images 102 of a blood vessel of one or more patients. The stent prediction apparatus 101 comprises a first stage 103 and a second stage 113 downstream of the first stage 103.

The first stage 103 is configured to access segmented parts of the one or more pre-stent intravascular images 102 including a lumen, a blood vessel wall, and calcifications. In some embodiments, the first stage 103 may comprise a deep learning segmentation model 602 configured to segment the one or more pre-stent intravascular images 102 to identify the segmented parts of the one or more pre-stent intravascular images 102. In some embodiments, the deep learning segmentation model 602 may be configured to use semantic segmentation. In other embodiments (not shown), segmentation of the one or more pre-stent intravascular images 102 may be performed outside of the first deep learning model 108 (e.g., by a remote computer) and the segmented parts may be provided to the first deep learning model 108.

One or more pre-stent metrics 105 are determined from segmented parts of the one or more pre-stent intravascular images 102. A plurality of image features 604 may also be extracted from the segmented parts of the one or more pre-stent intravascular images 102. In some embodiments, the plurality of image features 604 may comprise lumen features 604*a* (e.g., lesion percent stenosis, major axis length per frame, minor axis length per frame, eccentricity per frame, area, etc.), calcification features 604*b* (e.g., calcification arc angles, total length of calcification, average calcification depth in a frame, extent, solidity, etc.), intensity texture features 604*c*, or the like. In some embodiments, the plurality of image features 604 may further comprise first-order aggregation statistics (e.g., minimum, maximum, mean, median, SD, skewness, and kurtosis). In various embodiments, some of the plurality of image features 604 may be normalized, while others (e.g., lumen area) will not be, as the absolute area is important.

In various embodiments, the plurality of image features 604 may comprise two-dimensional (2D) features and/or three-dimensional (3D) features. In some embodiments, the plurality of image features 604 may comprise two-dimensional (2D) lumen features (e.g., 2D features extracted from the lumen), three-dimensional (3D) lumen features (e.g., 3D features extracted from the lumen), 2D calcification features (e.g., 2D features extracted from the one or more calcification lesions), and/or three-dimensional (3D) calcification features (e.g., 3D features extracted from the one or more calcification lesions). For example, in some embodiments the plurality of image features 604 may comprise 39 features including 12 two-dimensional lumen features, 6 three-dimensional lumen features, 12 two-dimensional calcification features, and 9 three-dimensional calcification features.

The first stage 103 further comprises a first deep learning model 108 that is configured to mimic finite element modeling (FEM) to generate one or more FEM-mimic simulations 112. A second stage 113 comprises a second deep learning model 114 that is configured to act upon the one or more FEM-mimic simulations 112 to generate stress/strain maps 324. In some embodiments, a plurality of FEM-mimic features 606 may be extracted from the one or more FEM-mimic simulations 112 and/or the stress/strain maps 324. The plurality of FEM-mimic features 606 may include lumen features 606*a* (e.g., area and eccentricity), vessel wall strain features 606*b* (e.g., a maximum, an average, and/or a standard deviation of strain in a calcification lesion), and vessel wall stress features 606*c* (e.g., a maximum, an average, and/or a standard deviation of stress in a calcification lesion).

The stent prediction apparatus 101 further comprises a machine learning model 612 configured to act upon the image features 604 and the FEM-mimic features 606 to generate a lumen area 614. In some embodiments, the machine learning model 612 is configured to predict the lumen area 614 at each frame using a sliding segmental analysis. The lumen area 614 at each frame will be processed to obtain a stent effectiveness metric 616 comprising standard stent deployment measures (e.g., SEI and MEI). In some embodiments, the machine learning model 612 may comprise a regression model, such as a Gaussian process regression, a random forest regressor, a gradient boosting regressor, an elastic net regressor, a least absolute shrinkage and selection operator regressor, or the like. In various embodiments, the regression model may be subject to 5-fold cross validation, feature selection, and hyper-parameter optimization, followed by evaluation on a held-out test set.

In some embodiments, an integrated feature reduction technique 608 may be used to identify discriminative features 610 that are provided to the machine learning model 612. In some embodiments, the integrated feature reduction technique 608 may comprise a least absolute shrinkage and selection operator (LASSO) used to identify the discriminative features 610. In such embodiments, the selection method applies a shrinking (regularization) process in which it assigns weights to regression variables. LASSO shrinks the regression coefficients toward 0 to eliminate irrelevant features from a regression model. In other embodiments, the integrated feature reduction technique 608 may comprise an elastic net algorithm used to identify the discriminative features 610. In yet other embodiments, the integrated feature reduction technique 608 may utilize a most relevant collective features obtained from methods such as heat map analysis and/or mRMR (minimum-redundancy-maximum relevance).

In some embodiments, the stent effectiveness metric 616 may comprise a stent expansion index (SEI) comprising a ratio of a post-stent lumen area of a blood vessel and a reference area of the blood vessel (e.g., an area associated with one or more parts of the blood vessel that are substantially free of calcification lesions). In additional embodiments, the stent effectiveness metric 616 may comprise a minimum SEI (MEI). In such embodiments, a plurality of SEIs are determined for a plurality of frames extending along a blood vessel (e.g., a first SEI is determined for a first frame of a blood vessel, a second SEI is determined for a second frame of a blood vessel, etc.) by dividing a post-stent lumen area of a blood vessel for a frame by the reference area of the blood vessel. The MEI is a smallest (e.g., minimum) one of the plurality of SEIs (e.g., the MEI is a smallest ratio of the post-stent lumen area and the reference area of the blood vessel).

Figure 7A:
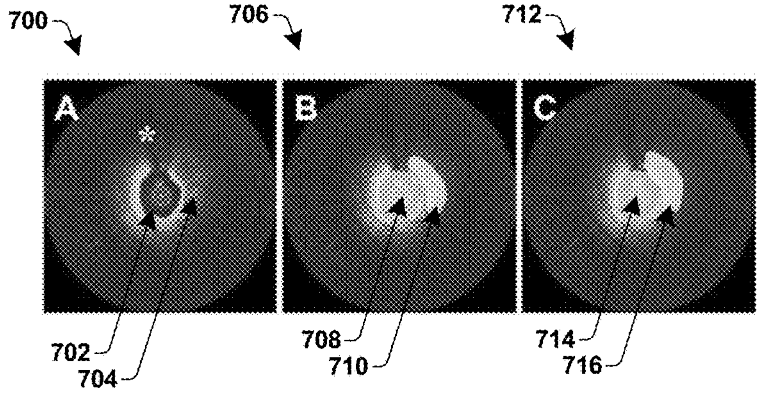
FIGS. 7A-7B illustrate cross-sectional and three-dimensional views of a blood vessel showing some examples of a segmentation of a blood vessel.
Figure 7B:
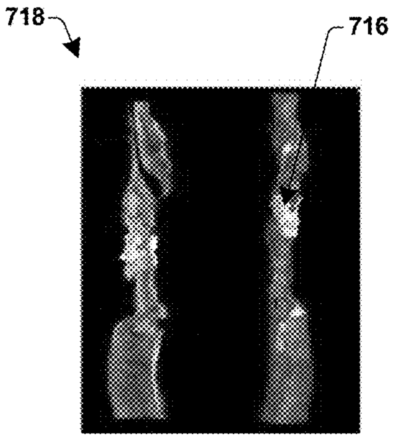

FIG. 7A illustrates cross-sectional views of a blood vessel showing a segmentation of the blood vessel (e.g., according to deep learning segmentation model 602 of FIG. 6).

Cross-sectional view 700 illustrates a cross-sectional view of a blood vessel prior to segmentation. The blood vessel comprises a lumen 702 surrounded in-part by a calcification lesion 704. Cross-sectional view 706 illustrates a cross-sectional view of a manually segmented blood vessel. The manual segmentation identifies a lumen 708 extending through the blood vessel and a calcification lesion 710 surrounding a part of the lumen. Cross-sectional views 712 illustrates a cross-sectional view of an automated segmented blood vessel. The automated segmentation identifies a lumen 714 extending through the blood vessel and a calcification lesion 716 surrounding a part of the lumen.

As can be seen by comparison of cross-sectional view 706 and cross-sectional view 712, there is good agreement between the manual segmentation and the automated segmentation. For example, quantitative assessments (e.g., of a lumen area, calcium angle, calcium thickness, etc.) may achieve deviations of less than approximately 4% between manual and automated segmentation. In some embodiments, a sensitivity of calcifications between the manual and automated segmentation may be approximately 89.5%, while a specificity may be approximately 94.2%.

FIG. 7D illustrates a three-dimensional view 718 of segmented blood vessels formed according to the automated segmentation. The three-dimensional view 718 shows the calcification lesion 716 over a length of the blood vessels.

Figure 8:
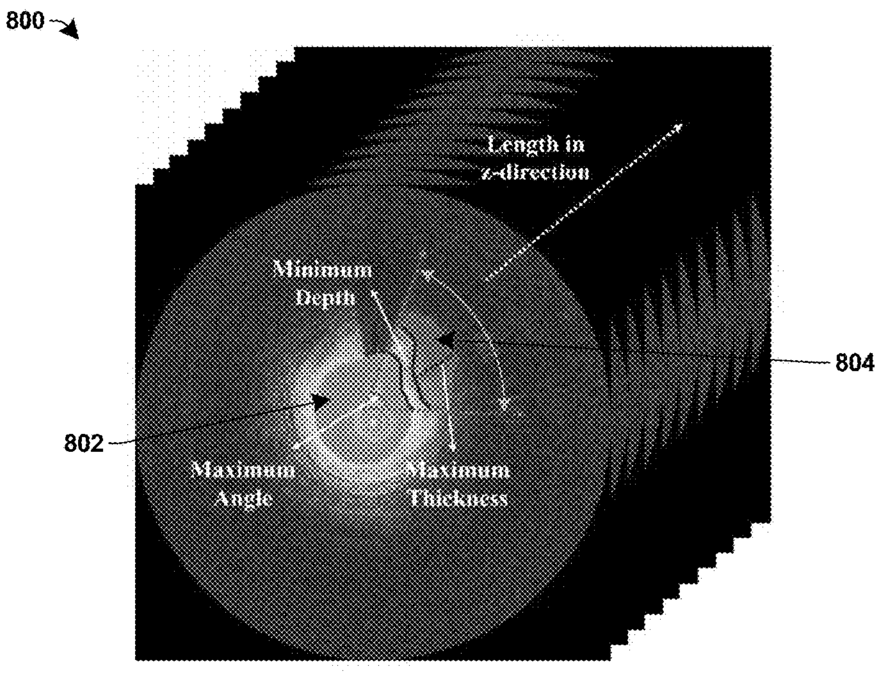
FIG. 8 illustrates a cross-sectional view showing some exemplary calcification features.

FIG. 8 illustrates a cross-sectional view 800 showing some exemplary calcification features.

Cross-sectional view 800 shows a calcification 802 arranged around a lumen 804 of a blood vessel. The cross-sectional view 800 illustrates calcification features (e.g., corresponding to calcification features 604*b* of FIG. 6) including a maximum calcification arc angle, a total length of calcification (in z-direction), a maximum thickness, and a minimum depth. Other features that may be obtained from the cross-sectional view include, but are not limited to, an average calcification depth in a frame, an extent, and a solidity.

Figure 9A:
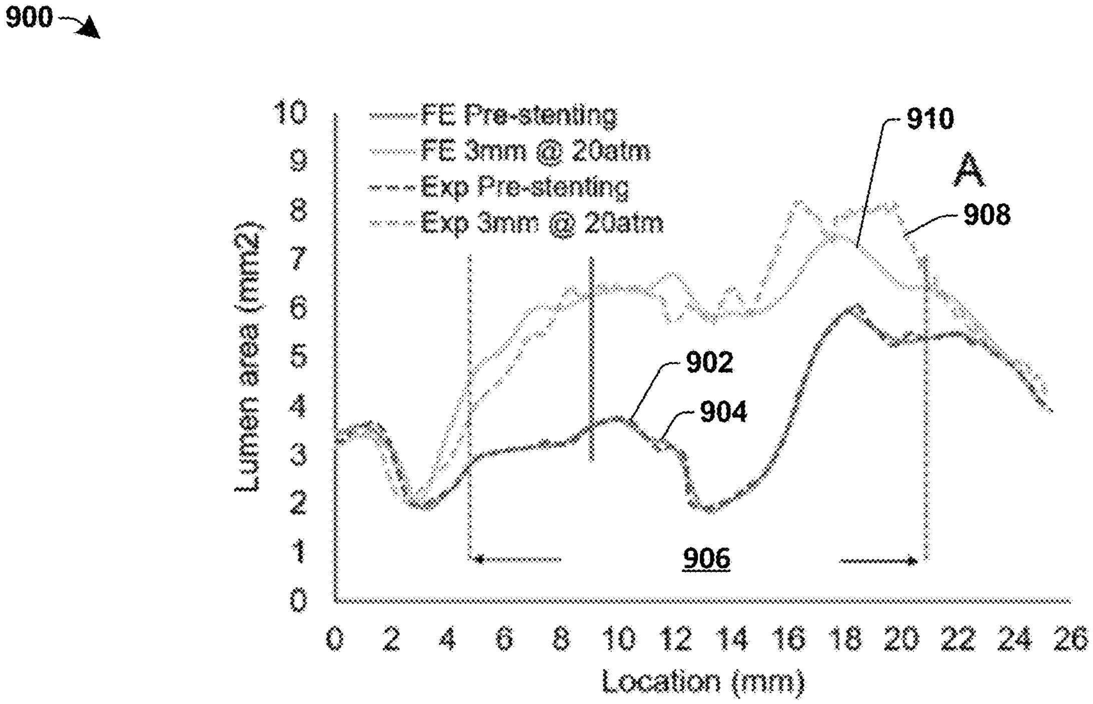
FIGS. 9A-9B illustrate graphs showing examples of comparisons of lumen areas along a blood vessel obtained using the disclosed stent prediction apparatus and by experiment.

FIG. 9A illustrates a line graph 900 showing examples of comparisons lumen areas (e.g., corresponding to lumen area 614 of FIG. 6) along a blood vessel obtained using the disclosed stent prediction apparatus and by experiment.

Line graph 900 shows a first pre-stent lumen area 902 (e.g., an actual lumen area) determined by an experiment over a length of a blood vessel and a second pre-stent lumen area 904 determined from a FEM-mimic simulation over a length of a blood vessel. A comparison of lumen areas along the length of the blood vessel, shows good agreement between the first pre-stent lumen area 902 and the second pre-stent lumen area 904. Line graph 900 also shows a stented region 906 within the blood vessel. Within a stented region 906, there is good agreement between a first post-stent lumen area 908 measured during an experiment (e.g., measured from a cadaver) and a second post-stent lumen area 910 calculated by the disclosed deep learning model.

Figure 9B:
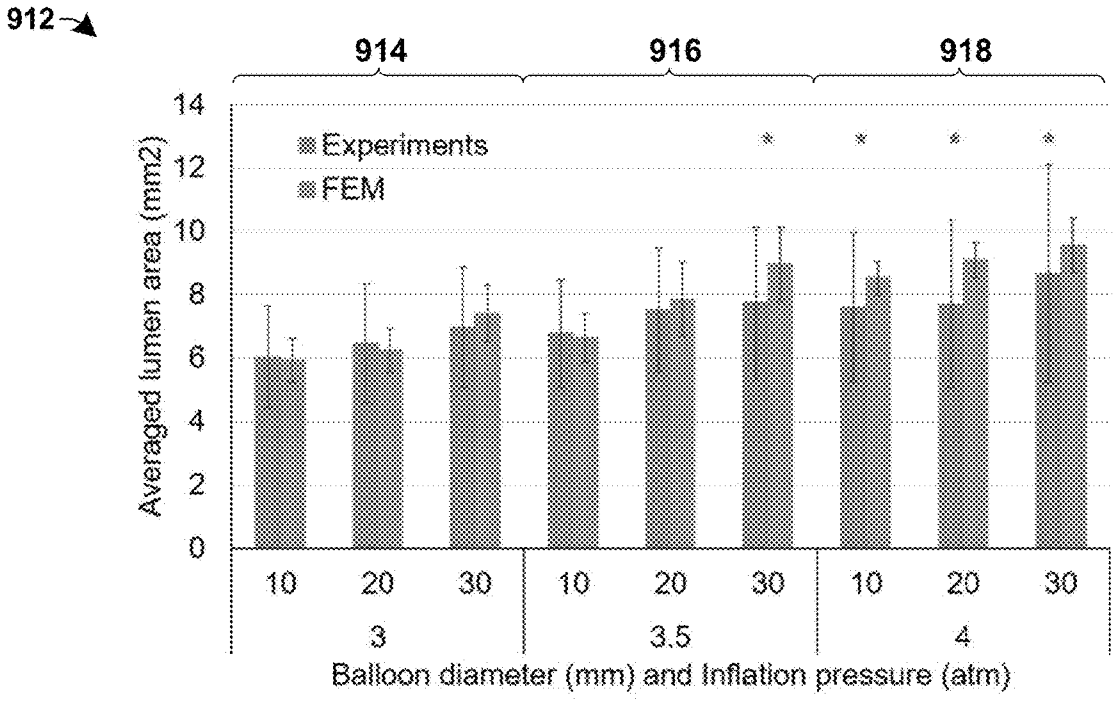

FIG. 9B illustrates a bar graph 912 showing examples of comparisons of lumen areas (e.g., corresponding to lumen area 614 of FIG. 6) along a blood vessel obtained using the disclosed stent prediction apparatus and by experiment.

Bar graph 912 shows averaged lumen areas for different balloon diameters and different inflation pressures. For example, within region 914, bar graph 912 shows average lumen areas obtained from experimentation and from a disclosed FEM-mimic simulation for a balloon diameter of 3 mm and for pressures of 10 atm, 20 atm and 30 atm. Within region 916, average lumen areas obtained from experimentation and from a disclosed FEM-mimic simulation are shown for a balloon diameter of 3.5 mm and for pressures of 10 atm, 20 atm and 30 atm. Within region 918, average lumen areas obtained from experimentation and from a disclosed FEM-mimic simulation are shown for a balloon diameter of 4 mm and for pressures of 10 atm, 20 atm and 30 atm. Bar graph 912 shows good agreement between the disclosed stent prediction apparatus and by experiment, especially at low pressure and/or balloon sizes.

Figure 10:
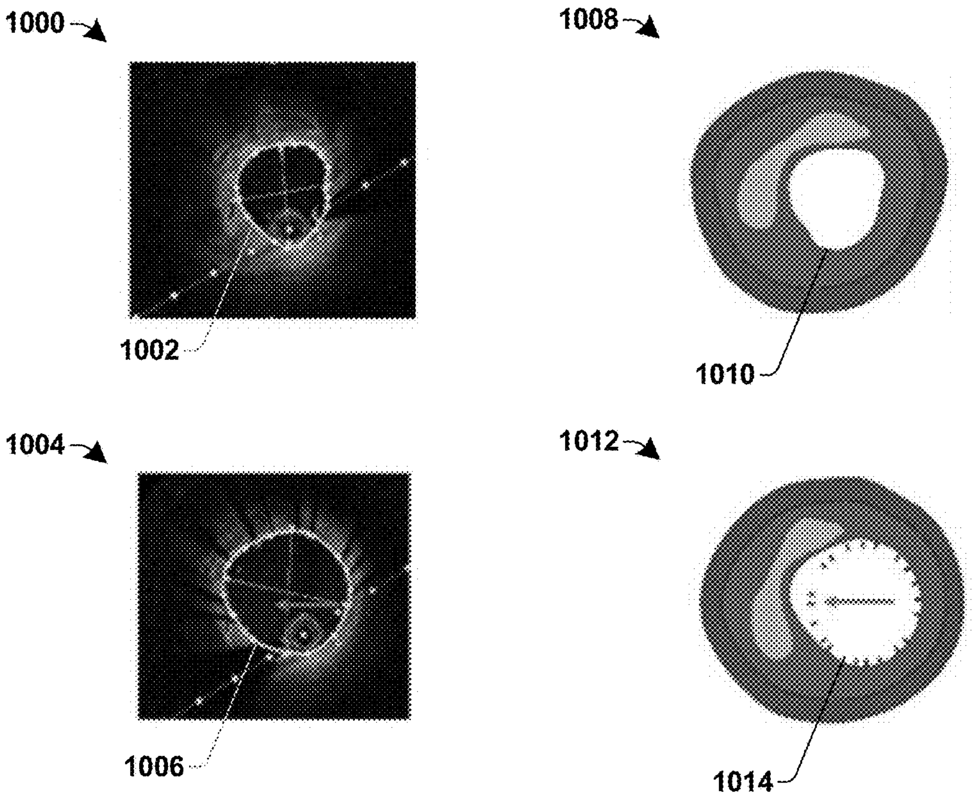
FIG. 10 illustrates cross-sectional views showing exemplary comparisons of lumen shapes obtained using the disclosed stent prediction apparatus and by experiment.

FIG. 10 illustrates cross-sectional views showing exemplary comparisons of lumen shapes obtained using the disclosed stent prediction apparatus and by experiment.

Cross-sectional view 1000 illustrates an IVOCT image of a blood vessel prior to stenting. As can be seen in cross-sectional view 1000, the blood vessel has a lumen 1002 with a first shape. Cross-sectional view 1004 illustrates an IVOCT image of a blood vessel after dilation (e.g., using a 3 mm balloon at a pressure of 20 atm). As can be seen in cross-sectional view 1004, the blood vessel has a lumen 1006 with a second shape that is different than the first shape.

Cross-sectional view 1008 illustrates a FEM-mimic simulation of a blood vessel prior to stenting. As can be seen in cross-sectional view 1008, the blood vessel has a lumen 1010 with a third shape. The third shape is shows good agreement with the first shape from the IVOCT image shown in cross-sectional view 1000. Cross-sectional view 1012 illustrates a FEM-mimic simulation of a blood vessel after dilation (e.g., using a 3 mm balloon at a pressure of 20 atm). As can be seen in cross-sectional view 1012, the blood vessel has a lumen 1014 with a fourth shape that is different than the third shape. The fourth shape is shows good agreement with the second shape from the IVOCT image shown in cross-sectional view 1004. Comparison of cross-sectional view 1004 and cross-sectional view 1012 show that the disclosed stent prediction apparatus is able to accurately capture changes in lumen shape. For example, in some embodiments predicted lumen areas achieved from a FEM-mimic simulation were within 0.07+/−0.05 $mm^2$ of predicted lumen areas achieved from experiment. In some embodiments, the disclosed stent prediction apparatus may also be able to accurately capture malapposition of stent structures.

FIGS. 11A-11D illustrates some exemplary results of the disclosed stent prediction apparatus.

Figure 11A:
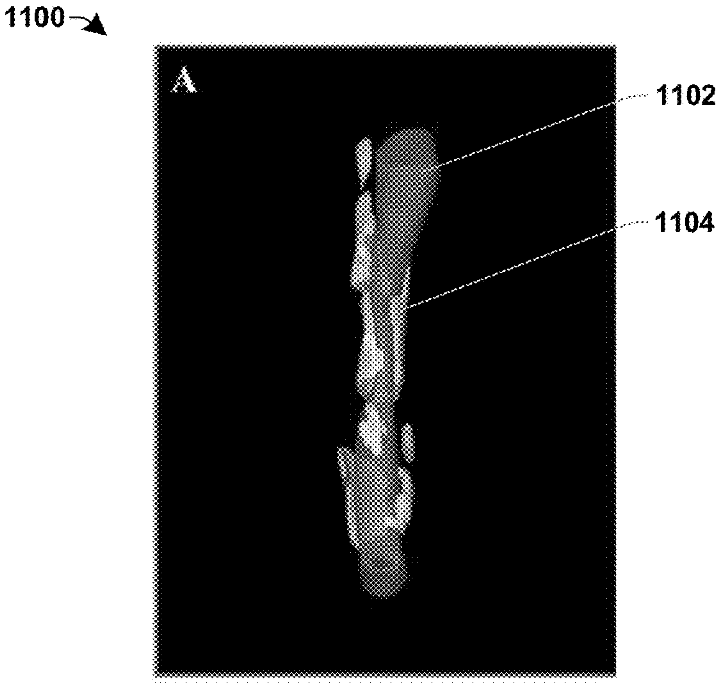
FIGS. 11A-11D illustrate some exemplary results of a disclosed stent prediction apparatus.

FIG. 11A illustrates a three-dimensional rendering 1100 showing an example of a blood vessel 1102 with calcifications 1104 formed from a FEM-mimic simulation.

Figure 11B:
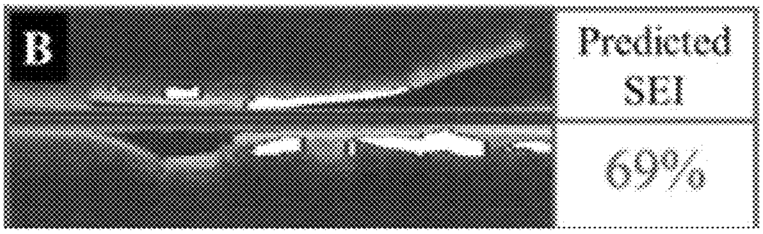

FIG. 11B illustrates a cross-sectional view 1106 taken along the blood vessel before stenting. The cross-sectional view 1106 is formed from the FEM-mimic simulation. The cross-sectional view 1106 corresponds to a predicted SEI of approximately 0.611.

Figure 11C:
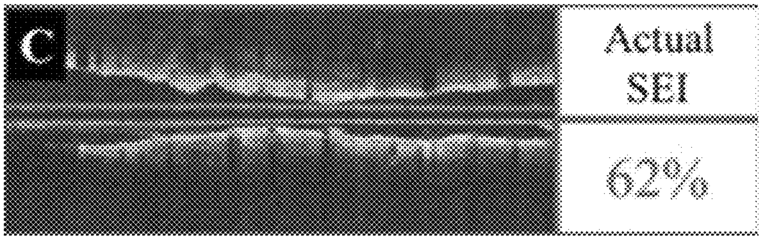

FIG. 11C illustrates a cross-sectional view 1108 taken along the blood vessel after stenting. The cross-sectional view 1108 is formed from an actual blood vessel. The cross-sectional view 1108 corresponds to a measured SEI of approximately 0.62.

Figure 11D:
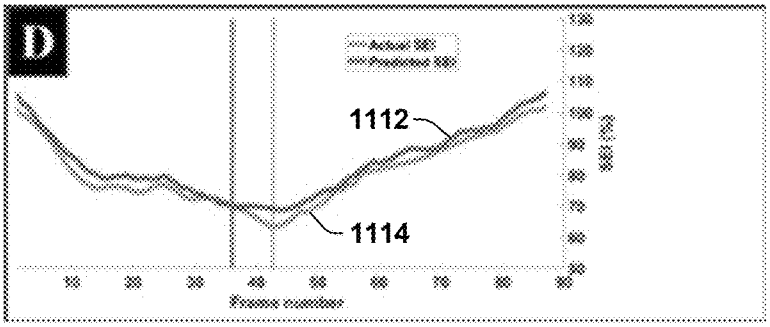

FIG. 11D illustrates a graph 1110 showing a first curve 1112 corresponding to a SEI predicted by a disclosed stent prediction apparatus and a second curve 1114 corresponding to a measured SEI. The first curve 1112 and the second curve 1114 have many similarities, including locations of lumen and minima, thereby suggesting good predictive value of the disclosed stent prediction apparatus in predicting SEI.

Figure 12:
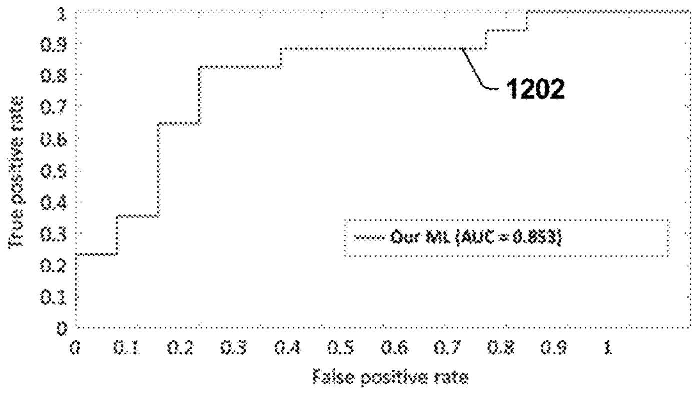
FIG. 12 illustrates a graph showing an exemplary receiver operating characteristic (ROC) curve corresponding to a disclosed stent prediction apparatus.

FIG. 12 illustrates a graph 1200 showing examples of a receiver operating characteristic (ROC) curve 1202 for prediction of stent expansion. The ROC curve 1202 has an area under curve (AUC) of approximately 0.853, thereby indicating good agreement with measured results.

Figure 13:
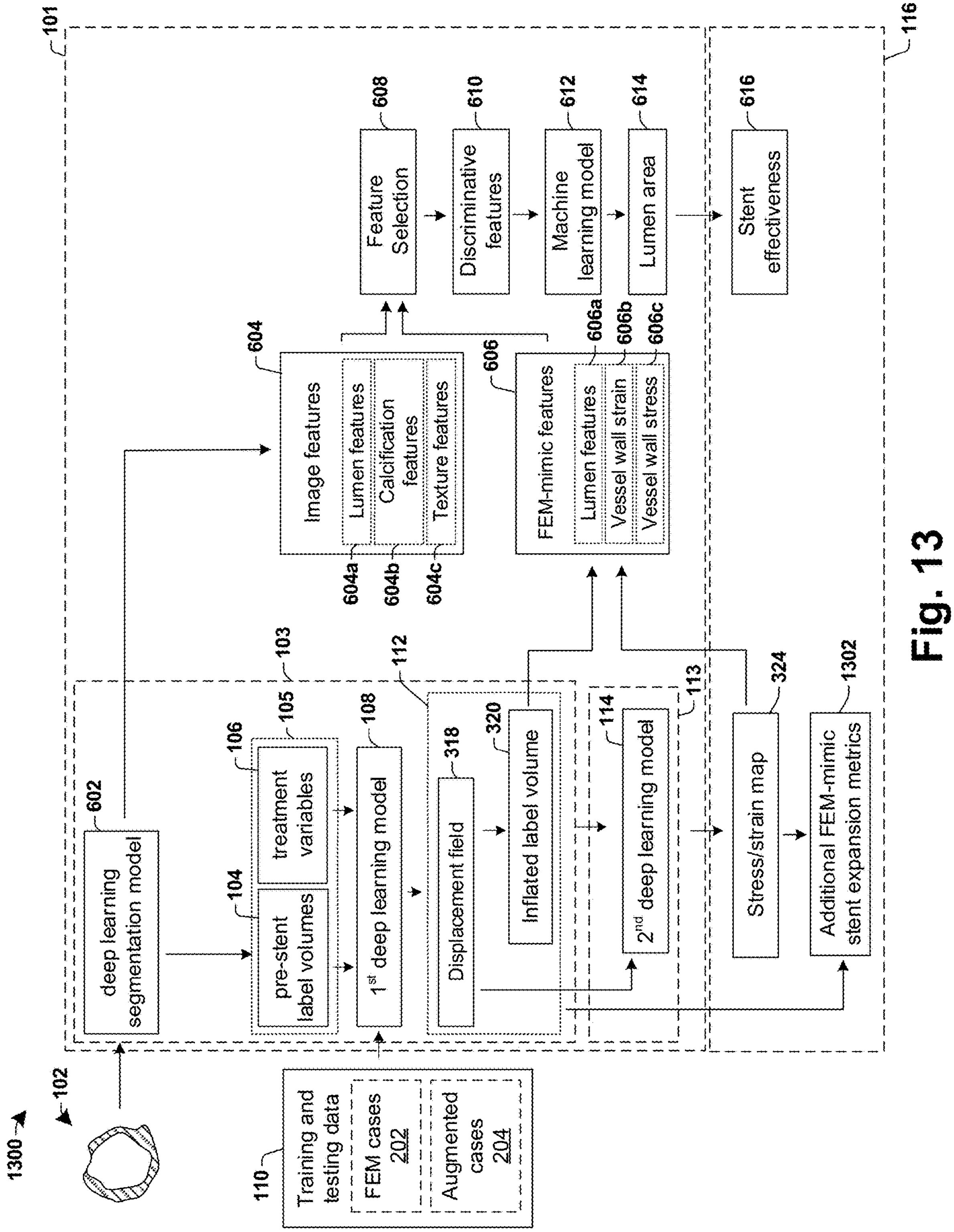
FIG. 13 illustrates a block diagram corresponding to some additional embodiments of a method and/or apparatus of determining a stent effectiveness using a deep learning model that mimics FEM.

FIG. 13 illustrates a block diagram 1300 corresponding to some additional embodiments of a stent prediction apparatus configured to determine a stent effectiveness using a deep learning model that mimics finite element modeling predictions.

The stent prediction apparatus 101 is configured to access an image volume comprising one or more pre-stent intravascular images 102 of a blood vessel of one or more patients. The stent prediction apparatus 101 comprises a first stage 103 and a second stage 113.

The first stage 103 comprises a first deep learning model 108 that is configured to mimic finite element modeling to generate one or more FEM-mimic simulations 112. The second stage 113 comprises a second deep learning model 114 that is configured to act upon the one or more FEM-mimic simulations 112 to generate stress/strain maps 324. In some embodiments, a plurality of FEM-mimic features 606 may be extracted from the one or more FEM-mimic simulations 112 and/or the stress/strain maps 324.

In some embodiments, one or more additional FEM-mimic stent expansion metrics 1302 may be extracted from the one or more FEM-mimic simulations 112 and/or the stress/strain maps 324. For example, in some embodiments the one or more additional FEM-mimic stent expansion metrics 1302 may comprise small histograms of calcification radial thicknesses. In other embodiments, the one or more additional FEM-mimic stent expansion metrics 1302 may comprise intensity texture features describing a "quality" of a calcification lesion. The intensity texture features can highlight appearances related to mechanical characteristics (e.g., micro-fractures following intravascular lithotripsy). In yet other embodiments, the one or more additional FEM-mimic stent expansion metrics 1302 may comprise a safe range of operation during a stent insertion procedure. For example, the stress/strain maps 324 may be compared to predetermined stress/strain threshold to determine a value of balloon pressure that may be used to avoid damage to a blood vessel (e.g., vascular tissue dissection, a ruptured blood vessel, a perforated blood vessel wall, and/or the like) or a balloon.

The one or more additional FEM-mimic stent expansion metrics 1302 may allow for the disclosed stent prediction apparatus 101 to make additional prognoses that may be useful to an interventional cardiologist in treating a patient. For example, it has been appreciated that treatment of some calcification lesions may utilize angioplasty or shockwave intravascular lithotripsy (IVL) to fracture a calcification lesion prior to stent implantation. By fracturing a calcification lesion, a subsequently implanted stent can expand smoothly. In some embodiments, the disclosed stent prediction apparatus 101 may compute stress and/or strain values from the stress/strain maps 324, and use the computed stress and/or strain values to determine whether a procedure will result in a calcification fracture that leads to good stent expansion.

Furthermore, the use of wrong operating parameters (e.g., balloon size and/or pressure) can not only fail fracture a calcification lesion but may also result in serious complications such as vessel rupture. In some embodiments, the disclosed stent prediction apparatus is configured to ensure that stent insertion parameters (e.g., balloon size and/or pressure) are well under the condition for vessel significant-dissection and/or rupture. In such embodiments, the disclosed stent prediction apparatus 101 is configured to compute stress values (e.g., a maximum stress) or strain values (e.g., a maximum strain) from the stress/strain maps 324. The stress values and the strain values are subsequently compared to a stress threshold or a strain threshold to determine if stent insertion parameters are likely to cause damage to a blood vessel (e.g., vessel significant-dissection and/or rupture in a vessel wall soft tissue).

Figure 14:
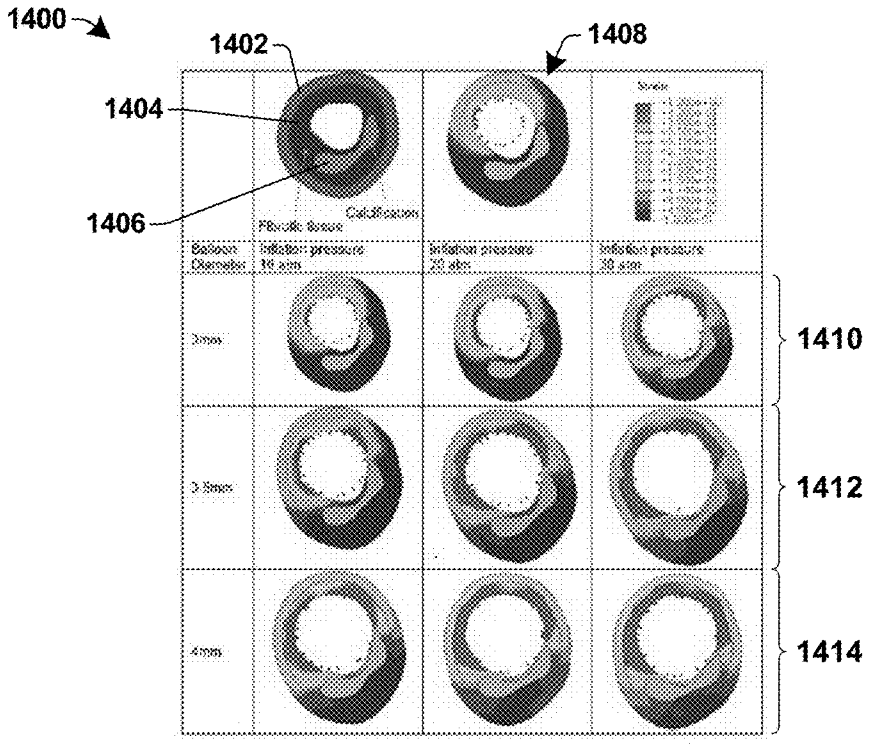
FIG. 14 illustrates exemplary cross-sectional views showing pre-stent and post-stent stress/strain maps for different balloon sizes and inflation pressures.

FIG. 14 illustrates cross-sectional views showing exemplary pre-stent and post-stent stress/strain maps for different balloon sizes and inflation pressures.

Cross-sectional view 1400 illustrates a stress/strain map of a blood vessel prior to stent implantation. The blood vessel comprises a vessel wall 1402 surrounding fibrotic tissue 1404. The fibrotic tissue 1404 further surrounds a calcification lesion 1406. Cross-sectional views 1408 shows a stress/strain map illustrating stresses and/or strains on the blood vessel after insertion of a stent.

In some embodiments, after insertion of a stent, one or more post-dilations may be performed. The one or more post-dilations may be performed by applying a higher pressure than that used during stent implantation. The one or more post-dilations help to ensure complete attachment between a stent and a vascular wall, thereby reducing a probability of in-stent thrombosis. Stress/strain maps 1410-1414 illustrate additional cross-sectional views of the blood vessel when acted upon with post-dilation balloons having different diameters and different balloon pressures (e.g., pressures of 10 atm, 20 atm, and 30 atm). The one or more post-dilations increase a stress and/or strain on the fibrotic tissue and vessel wall. Furthermore, with increasing balloon size and pressure, strain in tissue increases, giving lumen area increases and ultimately vessel rupture. However, the rigid calcification does not significantly change shape.

Figure 15:
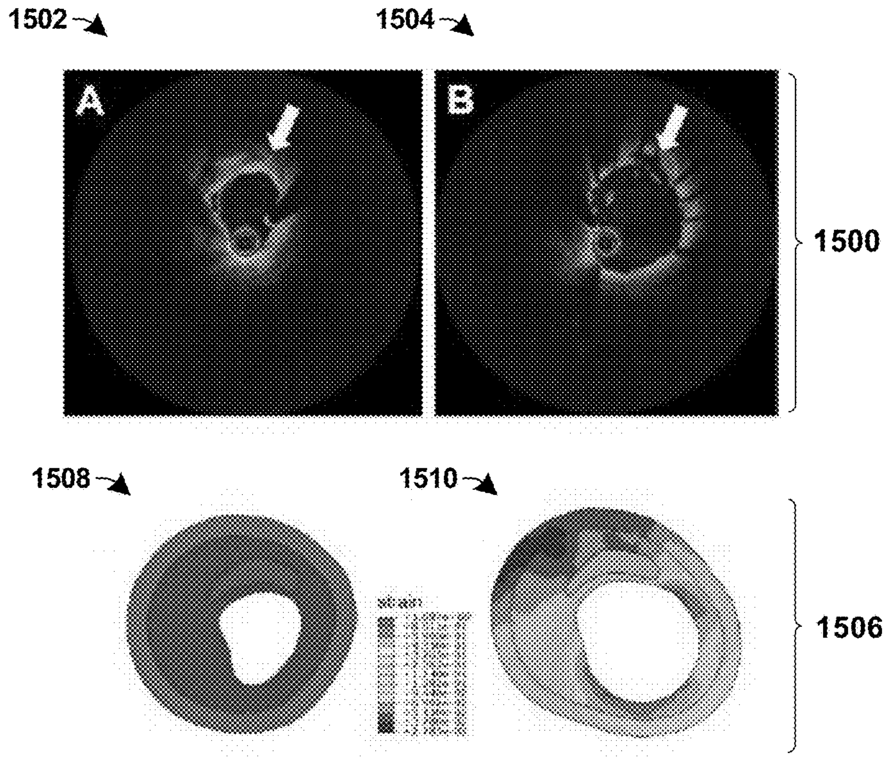
FIG. 15 illustrate exemplary stress/strain maps associated with balloon dilation leading to rupture.

FIG. 15 illustrates cross-sectional views showing some embodiments of strain and stress maps leading to vessel rupture.

Cross-sectional views 1500 show IVOCT images. Cross-sectional view 1502 shows a pre-stent IVCOT image. The yellow arrow in cross-sectional view 1502 shows a location of a future vessel rupture during dilation. Cross-sectional view 1504 shows an IVOCT image after balloon dilation (e.g., using a 3.5 mm balloon). The yellow arrow in cross-sectional view 1502 shows a location of a vessel rupture during dilation.

Cross-sectional views 1506 show stress/strain maps generated from FEM-mimic simulations. Cross-sectional view 1508 illustrates a stress/strain map prior to insertion of a stent. Cross-sectional view 1510 illustrates a stress/strain map after balloon dilation. As shown in cross-sectional view 1510, the stress/strain map shows a high strain at the point of rupture, thereby suggesting that the disclosed stress/strain maps can be used to accurately predict vessel rupture.

Figures 16, 17:
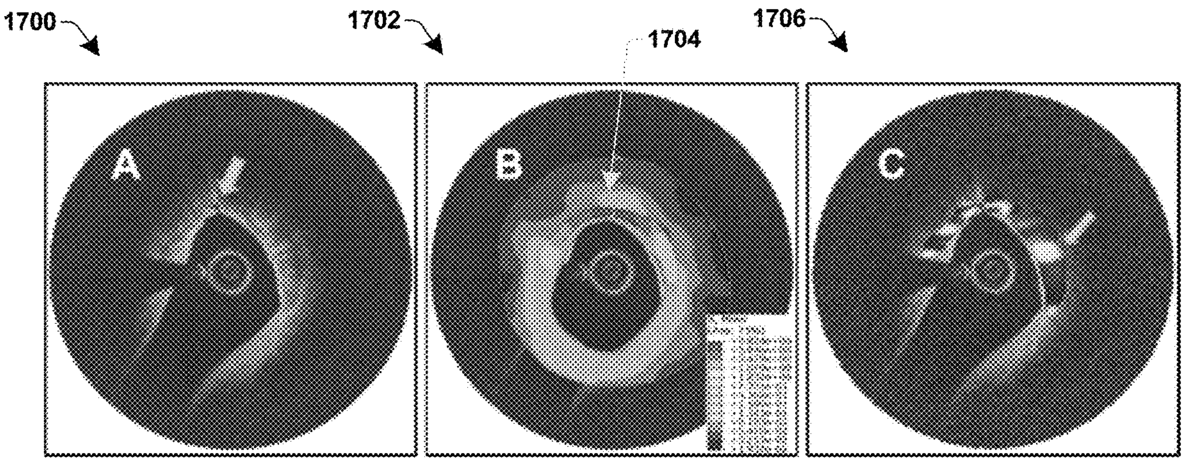
FIG. 16 illustrates a table showing some exemplary texture features of segmented parts of a segmented blood vessel.
FIG. 17 illustrates cross-sectional views showing stress/strain maps and texture features related to a blood vessel undergoing calcification fracture.

FIG. 16 illustrates a table 1600 showing some exemplary intensity texture features (e.g., corresponding to additional FEM-mimic stent expansion metrics 1302 of FIG. 13) of segmented parts of a segmented blood vessel.

Table 1600 shows some exemplary intensity texture features that describe a "quality" of a calcification. In various embodiments, the intensity texture features may include, but are not limited to, first order statistic features, 3D shaped based features, 2D shape-based features, Gray Level Cooccurrence Matrix features, Gray Level Run Length Matrix features, Gray Level Size Zone Matrix features, Neighboring Gray Tone Difference Matrix features, and/or Gray Level Dependence Matrix features.

Cross-sectional view 1700 shows an example of a blood vessel comprising a fracture of a large calcification (e.g., a calcification fracture) that occurs following intravascular lithotripsy (IVL) treatment. The yellow arrow in cross-sectional view 1700 indicates a location of a calcification fracture.

Cross-sectional view 1702 shows an exemplary FEM simulation showing a stress/strain map corresponding to the blood vessel. The stress/strain map predicts a high stress in an area 1704 that corresponds to a large calcification. The large stress gives rise to a simulated fracture (e.g., with a stress threshold of 10 MPa). A large calcification will result in higher strain (e.g., up to nearly 10 MPa) necessary to lead to fracture. Therefore, the stress/strain map illustrates an accurate prediction of the calcification fracture that is in good agreement with the IVOCT image of cross-sectional view 1700. This result demonstrates that stress/strain from FEM-mimic simulations can predict calcification fracture and that the disclosed stent prediction apparatus can accurately model pre-stent plaque modification interventions (e.g., IVL or atherectomy). Similar results may also be obtained in cases with high pressure treatments without pre-stent plaque modification. Therefore, as shown in cross-sectional view 1702, the disclosed FEM-mimic simulations can predict locations of potential calcification fractures.

Cross-sectional view 1706 shows intensity texture features extracted from a pre-stent image volume. As can be seen in cross-sectional view 1706, the highest variances in the intensity texture features are arranged at one or more locations corresponding to the calcification fracture. Therefore, the intensity texture features may also and/or alternatively be used by the disclosed stent prediction apparatus to provide for additional prognostic ability.

Figure 18:
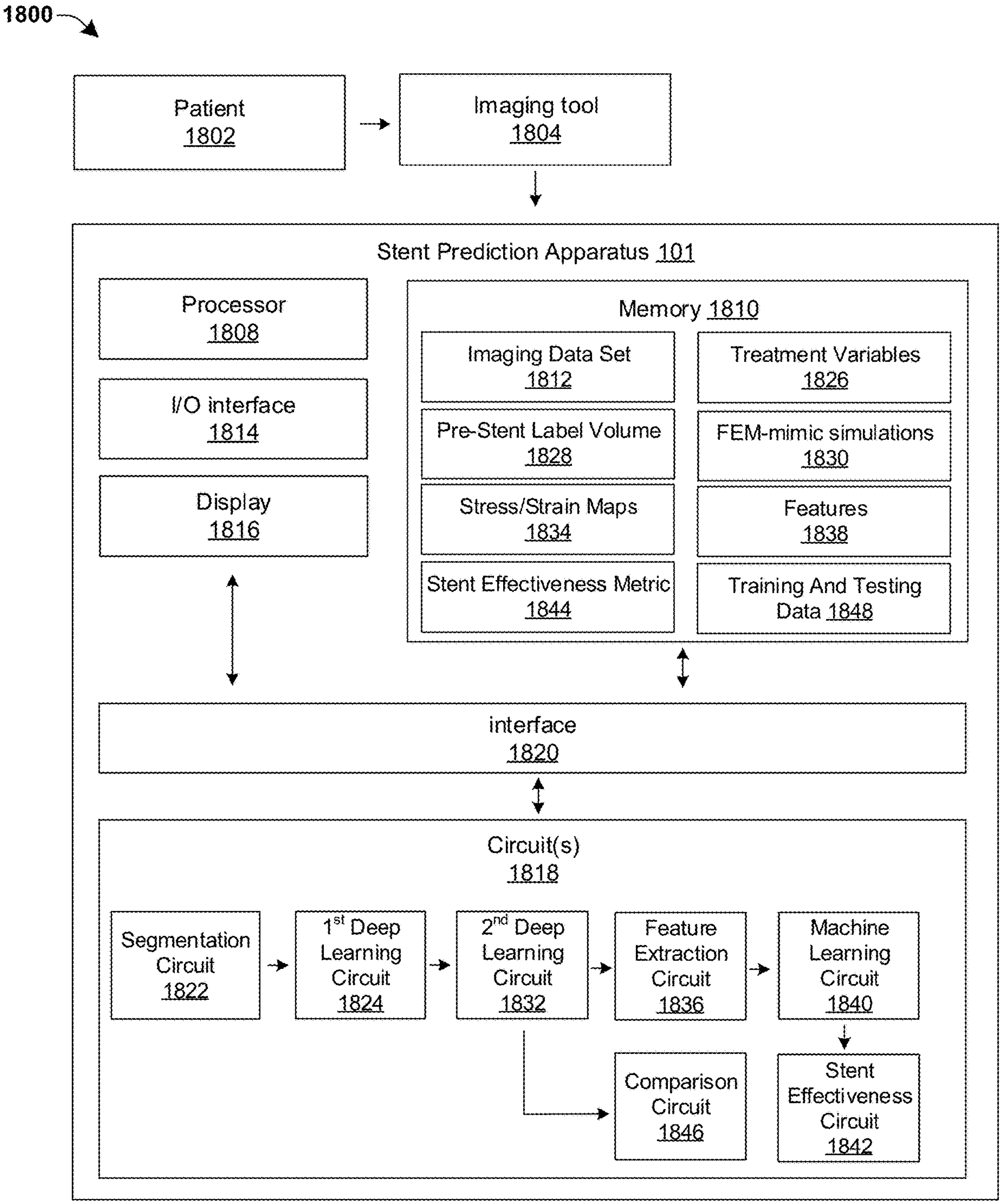
FIG. 18 illustrates a block diagram of some embodiments of an apparatus configured to determine a stent effectiveness using a deep learning model that mimics FEM.

FIG. 18 illustrates a block diagram of some embodiments of an apparatus 1800 configured to determine a stent effectiveness using a deep learning model that mimics FEM.

The apparatus 1800 comprises a stent prediction apparatus 101. The stent prediction apparatus 101 is coupled to an imaging tool 1804 that is configured to generate one or more pre-stent intravascular images of a patient 1802. In some embodiments, the imaging tool 1804 may comprise an IVOCT imaging system including a catheter that is configured to be inserted into a patient's blood vessel (e.g., artery) to obtain an IVOCT image of the blood vessel.

The stent prediction apparatus 101 comprises a processor 1808 and a memory 1810. The processor 1808 can, in various embodiments, comprise circuitry such as, but not limited to, one or more single-core or multi-core processors. The processor 1808 can include any combination of general-purpose processors and dedicated processors (e.g., graphics processors, application processors, etc.). The processor(s) 1808 can be coupled with and/or can comprise memory (e.g., memory 1810) or storage and can be configured to execute instructions stored in the memory 1810 or storage to enable various apparatus, applications, or operating systems to perform operations and/or methods discussed herein.

Memory 1810 can be configured to store an imaging data set 1812 comprising digitized images obtained by the imaging tool 1804 for a plurality of patients. The digitized images may comprise a plurality of pixels, each pixel having an associated intensity. In some additional embodiments, the digitized images may be stored in the memory 1810 as one or more training sets of digitized images for training a classifier and/or one or more validation sets (e.g., test sets) of digitized images.

The stent prediction apparatus 101 also comprises an input/output (I/O) interface 1814 (e.g., associated with one or more I/O devices), a display 1816, one or more circuits 1818, and an interface 1820 that connects the processor 1808, the memory 1810, the I/O interface 1814, the display 1816, and the one or more circuits 1818. The I/O interface 1814 can be configured to transfer data between the memory 1810, the processor 1808, the one or more circuits 1818, and external devices (e.g., imaging tool 1804).

In some embodiments, the one or more circuits 1818 may comprise hardware components. In other embodiments, the one or more circuits 1818 may comprise software components. The one or more circuits 1818 can comprise a segmentation circuit 1822 configured to perform a segmentation operation on one or more digitized images within the imaging data set 1812 to identify segmented parts of a blood vessel (e.g., a lumen, a calcification lesion, etc.). In some additional embodiments, the one or more circuits 1818 may further comprise a first deep learning circuit 1824. The first deep learning circuit 1824 is configured to act upon treatment variables 1826 associated with the one or more digitized images and a pre-stent label volume 1828 (e.g., including the segmented parts of the blood vessel) to generate one or more FEM-mimic simulations 1830 (e.g., including a displacement field, an inflated label volume, or the like). In some additional embodiments, the one or more circuits 1818 may further comprise a second deep learning circuit 1832 configured to utilize the one or more FEM-mimic simulations 1830 to generate one or more stress/strain maps 1834.

In some additional embodiments, the one or more circuits 1818 may further comprise feature extraction circuit 1836 configured to extract image features from the one or more digitized images within the imaging data set 1812 and to extract a FEM-mimic features from the FEM-mimic simulations 1830 and/or the stress/strain maps 1834. The image features and the FEM-mimic features may be stored in the memory 1810 as features 1838. A machine learning circuit 1840 is configured to operate upon the features 1838 to generate a lumen area. A stent effectiveness circuit 1842 may be further configured to utilize the lumen area to determine a stent effectiveness metric 1844 (e.g., a SEI, an MEI, or the like). In some embodiments, the circuits 1818 may further comprise a comparison circuit 1846 configured to utilizing the one or more stress/strain maps 1834 to predict potential damage to a blood vessel.

In some embodiments, the first deep learning circuit 1824, the second deep learning circuit 1832, and/or the machine learning circuit 1840 may be trained using training and testing data 1848 stored in the memory 1810. In some such embodiments, the training and testing data 1848 may comprise FEM simulations. The training and testing data 1848 may be separated into a training set, a testing set, and/or a validation set.

Therefore, the present disclosure relates to a method and/or apparatus to determine a stent effectiveness using a deep learning model that mimics finite element modeling (FEM) based on one or more pre-stent intravascular images.

In some embodiments, the present disclosure relates to a method of determining a stent effectiveness, including accessing a pre-stent intravascular image of a blood vessel of a patient; determining one or more pre-stent label volumes of the blood vessel; determining one or more treatment variables associated with the pre-stent intravascular image; generating one or more FEM-mimic simulations by applying a first deep learning model to the one or more pre-stent label volumes and the one or more treatment variables; and utilizing the one or more FEM-mimic simulations to determine a stent effectiveness metric.

In other embodiments, the present disclosure relates to a non-transitory computer-readable medium storing computer-executable instructions that, when executed, cause a processor to perform operations, including accessing an intravascular optical coherence tomography (IVOCT) image of a blood vessel;

- determining one or more pre-stent label volumes associated with the blood vessel;
- determining one or more treatment variables associated with the blood vessel;
- generating one or more FEM-mimic simulations by applying a first deep learning model to the one or more pre-stent label volumes and the one or more treatment variables, the one or more FEM-mimic simulations including a displacement field and one or more inflated label volumes formed using the displacement field and the one or more pre-stent label volumes; and generating one or more stress/strain maps from one or more of the displacement field and the one or more inflated label volumes.

In yet other embodiments, the present disclosure relates to a stent prediction apparatus, including a memory configured to stores a pre-stent intravascular image of a blood vessel of a patient, one or more treatment variables relating to the pre-stent intravascular image, and one or more pre-stent label volumes of the pre-stent intravascular image; a first deep learning model configured to generate one or more FEM-mimic simulations from the one or more treatment variables and the one or more pre-stent label volumes; and a second deep learning model configured to generate one or more stress/strain maps from the one or more FEM-mimic simulations.

Examples herein can include subject matter such as an apparatus, including a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system according to embodiments and examples described. References to “one embodiment”, “an embodiment”, “one example”, and “an example” indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase “in one embodiment” does not necessarily refer to the same embodiment, though it may.

“Computer-readable storage device”, as used herein, refers to a device that stores instructions or data. “Computer-readable storage device” does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

“Circuit”, as used herein, includes but is not limited to hardware, firmware, software in execution on a machine, or combinations of each to perform a function(s) or an action (s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term “includes” or “including” is employed in the detailed description or the claims, it is intended to be inclusive in a manner similar to the term “comprising” as that term is interpreted when employed as a transitional word in a claim.

Throughout this specification and the claims that follow, unless the context requires otherwise, the words ‘comprise’ and ‘include’ and variations such as ‘comprising’ and ‘including’ will be understood to be terms of inclusion and not exclusion. For example, when such terms are used to refer to a stated integer or group of integers, such terms do not imply the exclusion of any other integer or group of integers.

To the extent that the term “or” is employed in the detailed description or claims (e.g., A or B) it is intended to mean “A or B or both”. When the applicants intend to indicate “only A or B but not both” then the term “only A or B but not both” will be employed. Thus, use of the term “or” herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method of determining a stent effectiveness, comprising:

- accessing a pre-stent intravascular image of a blood vessel of a patient;
- determining one or more pre-stent label volumes of the blood vessel;
- determining one or more treatment variables associated with the pre-stent intravascular image;
- generating one or more FEM-mimic simulations by applying a first deep learning model to the one or more pre-stent label volumes and the one or more treatment variables;
- applying the first deep learning model to the one or more pre-stent label volumes and the one or more treatment variables to form a displacement field showing changes in positions of blood vessel components in response to insertion and expansion of a stent at the one or more treatment variables;

determining one or more inflated label volumes using the displacement field and the one or more pre-stent label volumes;

generating one or more stress/strain maps from one or more of the displacement field and the one or more inflated label volumes; and utilizing the one or more FEM-mimic simulations to determine a stent effectiveness metric.

2. The method of claim 1, wherein the one or more FEM-mimic simulations comprise the displacement field and the one or more inflated label volumes.

3. The method of claim 2, wherein the one or more stress/strain maps are formed using a second deep learning model.

4. The method of claim 2, further comprising:

utilizing the one or more stress/strain maps to predict potential damage to the blood vessel.

5. The method of claim 1, further comprising:

accessing segmented parts of the pre-stent intravascular image;

extracting a plurality of image features from the segmented parts and a plurality of FEM-mimic features from the one or more FEM-mimic simulations;

determining a lumen area from one or more of the plurality of image features and the plurality of FEM-mimic features; and determining a stent expansion index (SEI) or a minimum expansion index (MEI) from the lumen area.

6. The method of claim 5, selecting discriminative features from the plurality of image features and the plurality of FEM-mimic features; and providing the discriminative features to a regression model configured to determine the SEI or the MEI.

7. The method of claim 1, wherein the one or more FEM-mimic simulations are generated for a center frame using inputs collected from surrounding frames within a distance of the center frame.

8. The method of claim 1, wherein the pre-stent intravascular image comprises one or more optical coherence tomography (IVOCT) images.

9. A non-transitory computer-readable medium storing computer-executable instructions that, when executed, cause a processor to perform operations, comprising:

accessing an intravascular optical coherence tomography (IVOCT) image of a blood vessel;

determining one or more pre-stent label volumes associated with the blood vessel;

determining one or more treatment variables associated with the blood vessel;

generating one or more FEM-mimic simulations by applying a first deep learning model to the one or more pre-stent label volumes and the one or more treatment variables, wherein the one or more FEM-mimic simulations include a displacement field showing changes in positions of blood vessel components in response to insertion and expansion of a stent at the one or more treatment variables and one or more inflated label volumes formed using the displacement field and the one or more pre-stent label volumes; and generating one or more stress/strain maps from one or more of the displacement field and the one or more inflated label volumes.

10. The non-transitory computer-readable medium of claim 9, wherein the operations further comprise:

extracting one or more image features from the IVOCT image;

extracting one or more FEM-mimic features from the one or more FEM-mimic simulations; and predicting a stent effectiveness from the one or more image features and the one or more FEM-mimic features.

11. The non-transitory computer-readable medium of claim 10, wherein the one or more FEM-mimic features comprise lumen features, vessel wall strain features, and vessel wall stress features.

12. The non-transitory computer-readable medium of claim 9, wherein the one or more stress/strain maps are formed using a second deep learning model.

13. The non-transitory computer-readable medium of claim 9, wherein the operations further comprise:

comparing stress values or strain values obtained from the one or more stress/strain maps to a predetermined stress/strain threshold to predict potential damage to the blood vessel.

14. The non-transitory computer-readable medium of claim 9, wherein the operations further comprise:

determining a plurality of features from the IVOCT image and from the one or more FEM-mimic simulations;

operating a machine learning model on the plurality of features to determine a lumen area from one or more of the plurality of features; and determining a stent effectiveness from the lumen area.

15. The non-transitory computer-readable medium of claim 9, wherein the operations further comprise:

training the first deep learning model by comparing the displacement field to training and testing data generated by a finite element model.

16. The non-transitory computer-readable medium of claim 15, wherein a loss function is used to compare the displacement field to the training and testing data.

17. A stent prediction apparatus, comprising:

a memory configured to store a pre-stent intravascular image of a blood vessel of a patient, one or more treatment variables relating to the pre-stent intravascular image, and one or more pre-stent label volumes of the pre-stent intravascular image;

a first deep learning model configured to generate one or more FEM-mimic simulations from the one or more treatment variables and the one or more pre-stent label volumes by:

applying the first deep learning model to the one or more pre-stent label volumes and the one or more treatment variables to form a displacement field showing changes in positions of blood vessel components in response to insertion and expansion of a stent at the one or more treatment variables; and determining one or more inflated label volumes using the displacement field and the one or more pre-stent label volumes; and a second deep learning model configured to generate one or more stress/strain maps from one or more of the displacement field and the one or more inflated label volumes.

18. The stent prediction apparatus of claim 17, further comprising:

a feature extraction circuit configured to extract a plurality of image features from the pre-stent intravascular image and to further extract a plurality of FEM-mimic features from the one or more FEM-mimic simulations and the one or more stress/strain maps; and a machine learning circuit configured to operate upon the plurality of image features and the plurality of FEM-mimic features to generate a lumen area.

19. The stent prediction apparatus of claim 18, further comprising:

a stent effectiveness circuit configured to utilize the lumen area to generate a stent effectiveness metric.

20. The stent prediction apparatus of claim 18, further comprising:

a comparison circuit configured to utilize the one or more stress/strain maps to predict potential damage to the blood vessel.

* * * * *